(12) United States Patent
Ranganathan et al.

(10) Patent No.: US 7,422,733 B2
(45) Date of Patent: Sep. 9, 2008

(54) LINKABLE SIALYL LEWIS X ANALOGS

(75) Inventors: Ramachandran Ranganathan, Kensington, CA (US); Kondareddiar Ramalingam, Dayton, NJ (US); Radhakrishua Pillai, Cranbury, NJ (US); Edmund E. Marinelli, Lawrenceville, NJ (US); Rolf E. Swenson, Princeton, NJ (US)

(73) Assignee: Bracco International B.V., Amsterdam (NL)

( * ) Notice: Subject to any disclaimer, the term of this patent is extended or adjusted under 35 U.S.C. 154(b) by 493 days.

(21) Appl. No.: 10/432,914

(22) PCT Filed: Nov. 29, 2001

(86) PCT No.: PCT/US01/44590

§ 371 (c)(1),
(2), (4) Date: Nov. 17, 2003

(87) PCT Pub. No.: WO02/062810

PCT Pub. Date: Aug. 15, 2002

(65) Prior Publication Data

US 2004/0097403 A1 May 20, 2004

Related U.S. Application Data

(60) Provisional application No. 60/250,238, filed on Nov. 29, 2000.

(51) Int. Cl.
*A61B 8/00* (2006.01)
*A61B 8/13* (2006.01)
*A61K 31/702* (2006.01)
*A61K 9/127* (2006.01)

(52) U.S. Cl. ............... 424/9.5; 424/9.51; 424/9.52; 424/450

(58) Field of Classification Search ........... 424/1.21, 424/1.73, 9.322, 9.323, 9.351; 514/24; 536/55.2
See application file for complete search history.

(56) References Cited

U.S. PATENT DOCUMENTS

| | | | | |
|---|---|---|---|---|
| 4,971,802 A | * | 11/1990 | Tarcsay et al. | 424/450 |
| 5,604,207 A | * | 2/1997 | DeFrees et al. | 514/25 |
| 5,665,329 A | * | 9/1997 | Ramalingam et al. | 424/1.65 |
| 5,697,902 A | * | 12/1997 | Goldenberg | 604/500 |
| 5,872,096 A | | 2/1999 | Venot et al. | 515/8 |
| 5,976,495 A | * | 11/1999 | Pollak et al. | 424/1.69 |
| 6,132,764 A | * | 10/2000 | Li et al. | 424/450 |
| 6,143,274 A | * | 11/2000 | Tweedle et al. | 424/1.65 |
| 6,331,289 B1 | * | 12/2001 | Klaveness et al. | 424/9.52 |

FOREIGN PATENT DOCUMENTS

| | | |
|---|---|---|
| WO | WO 92 22565 | 12/1992 |
| WO | WO 94 26770 | 11/1994 |

OTHER PUBLICATIONS

Wittmann, V. et al "Chemoenzymatic synthesis and fluorescent visualization . . . " Chem. Eur. J. (2000) vol. 6, No. 1, pp. 162-171.*
Andre, S. et al "Lactose-containing starburst dendrimers . . . " Glycobiology (1999) vol 9, No. 11, pp. 1253-1261.*
DeFrees, S. et al "Sialyl Lewis x liposomes as multivalent ligand . . . " JACS (1996) vol. 118, pp. 6101-6104.*
Palcic, M. et al "Chemoenzymatic synthesis of dendritic sialyl Lewis x." Carbohyd. Res. (1998) vol. 305, pp. 433-442.*
Hiruma, K. et al.; "Synthesis of Analogs of 1, 1-Linked Galactosyl Mannoside as Mimetics of Sialyl Lewis X Tetrasaccharide", Elsevier Science Publishers, Amsterdam, NL. vol. 54, No. 52, pp. 15781-15792, Dec. 24, 1998.
Kretzschmar, G. et al.: "Oligosaccharide Recognition by Selectins: Synthesis and Biological Activity of Multivalent Sialyl Lewis-X Ligans", Elsevier Science Publishers, Amsterdam, NL. vol. 51, No. 47, pp. 13015-13030, Nov. 20, 1995.
Thoma, G. et al.: "Synthesis and Biological Evaluation of a Sialyl Lewis X Mimic with Significantly Imrproved E-Selectin Inhibition", Bioorganic & Medicinal Chemistry Letters, Oxford, GB. vol. 11, No. 7, pp. 923-925, Apr. 9, 2001.
PCT International Search Report for PCT/US01/44590 dated Oct. 29, 2002.

* cited by examiner

*Primary Examiner*—Leigh C Maier
(74) *Attorney, Agent, or Firm*—Kramer Levin Naftalis & Frankel LLP

(57) ABSTRACT

Disclosed herein is a class of linkable tetrasaccharide compounds that includes the amino phenyl glycoside of sialyl Lewis X ($SLe^x$) and related analogs. These compounds have conjugatable nucleophilic groups, making them useful in preparing multimeric $SLe^x$ compositions. In particular, the disclosed $SLe^x$ compounds can be used to prepare selectin binding ligand conjugates by linking them to a reporter moiety, such as a contrast agent, a radiodiagnostic agent, or a cytotoxic or chemotherapeutic agent. The $SLe^x$ compounds and conjugates of the invention exhibit binding to selectin that is similar to native Sialyl $Le^x$, and are, therefore, useful for diagnosing and treating selectin-mediated disorders and related conditions.

13 Claims, No Drawings

US 7,422,733 B2

LINKABLE SIALYL LEWIS X ANALOGS

This application is the national stage filing of corresponding international application number PCT/US01/44590, filed Nov. 29, 2001, which claims priority of U.S. provisional application No. 60/250,238, filed Nov. 29, 2000.

FIELD OF THE INVENTION

The invention relates to linkable sialyl Lewis X (sialyl $Le^x$ or $SLe^x$) analogs and methods of using these compounds to treat inflammation and related disorders.

BACKGROUND OF THE INVENTION

The phenomenon of cellular adhesion plays an important role in the complex processes of inflammation and cancer metastasis. In response to injury and infection, damaged tissues release activating factors known as cytokines. The released cytokines signal vascular endothelial cells to change their shape and express cell adhesion proteins called selectins on their surfaces. The selectins promote the adhesion of leukocytes to the endothelium by binding to carbohydrate antigens, such as sialyl $Le^x$, that are present on the surface of leukocytes in the blood stream. The leukocytes then move past the endothelial cells, through the blood vessel wall, and into the areas of injury and infection, thereby establishing a foci of inflammation.

In certain situations, adhesion of leukocytes to the endothelium may be abnormal or excessive, resulting in tissue damage instead of repair. A number of inflammatory diseases and related disorders are characterized by aberrant cellular adhesion, including atherosclerosis, blood clotting, rheumatism, arthritis, psoriasis, dermatitis, cancer, reperfusion injuries, and infection. Thus, there is a need for inhibitors of the adhesion process that are capable of alleviating the symptoms associated with such conditions.

Analogs of sialyl $Le^x$ that exhibit enhanced binding characteristics to selectins are believed to block the leukocyte adhesion process and prevent the penetration of leukocytes into the injury site, thereby reducing or eliminating the symptoms associated with inflammation. Recent efforts have been made to develop $SLe^x$ analogs with improved binding properties. The binding of monomeric $SLe^x$ analogs to E-selectin and L-selectin is generally weak (i.e. only in the range of 1-2 mm), often making them unsuitable for many applications, including targeting. The binding of bridged, dimeric sialyl $Le^x$ analogs, however, was reported to be about 5 fold greater than the monomer, depending upon the nature of the bridge connecting the two monomers. Multivalent liposomic sialyl $Le^x$ mimetics have been shown to exhibit up to a 100 fold greater binding strength than controls in selectin-mediated cell adhesion inhibition assays. Furthermore, a sialyl $Le^x$-PEG-DSPE derivative that was incorporated into PEG grafted liposomes was shown to be greater than 5000 fold more potent than the monomeric analog as an inhibitor of E-selectin mediated cellular adhesion in an ELISA assay.

SUMMARY OF THE INVENTION

The dramatic increase in binding strength exhibited by multivalent Sialyl $Le^x$ compositions as compared to monomeric analogs indicates that oligosaccharide multivalency enhances the ability of these compositions to inhibit selectin-mediated cellular adhesion. This amplified level of binding strength makes these multivalent compositions more effective as therapeutic agents and increases their usefulness in targeting applications.

The present invention provides a class of linkable tetrasaccharide compounds that includes the amino phenyl glycoside of sialyl Lewis X and related analogs. These compounds have conjugatable nucleophilic amino groups, making them useful in preparing multimeric $SLe^x$ compositions. The compounds of the invention also exhibit binding to selectin that is superior to native Sialyl $Le^x$, and may be used as a means for treating inflammation and related disorders by inhibiting selectin-mediated cellular adhesion.

The invention also features selectin binding ligand conjugates that include (1) a $SLe^x$ analog moiety, (2) a linker, and (3) a reporter moiety. The reporter moiety generally includes a diagnostic imaging agent or a cytotoxic or therapeutic agent. In preferred embodiments, the reporter contains (a) one or more macrocyclic or non-macrocyclic metal chelating ligands that are optionally chelated to paramagnetic, superparamagnetic radioactive, or non-radioactive metals, (b) a phospholipid moiety, or (c) a cytotoxic or chemotherapeutic agent. Depending on the nature of the reporter moiety, the conjugates may be used as imaging agents for visualization of tissues using MRI, ultrasound, or radiodiagnostic techniques. The conjugates may also be used as radiotherapeutic, chemotherapeutic or cytotoxic agents, or as a means for treating inflammatory diseases, infection, and related disorders by inhibiting the cellular adhesion process.

The invention further provides pharmaceutical compositions that include a therapeutically effective amount of a $SLe^x$ analog or conjugate in combination with a pharmaceutically acceptable carrier. Suitable carriers include, but are not limited to, saline, buffered saline, dextrose, water, glycerol, ethanol, and combinations thereof. The composition can be adapted for the mode of administration and can be in the form of a pill, tablet, capsule, spray, powder, or liquid.

Other features and advantages of the invention will be apparent from the following detailed description thereof and from the claims.

DETAILED DESCRIPTION

In order to prepare multimeric Sialyl $Le^x$ compositions, we recognized that $SLe^x$ analogs having conjugatable end groups would be useful. We, therefore, developed a program for the synthesis of the aminophenyl glycoside of Sialyl $Lewis^x$ and related analogs. These compound have binding properties superior to native sialyl $Le^x$ and are useful in a wide range of applications.

Sialyl $Lewis^x$ Analogs

The structure of sialyl Lewis X is shown below as Formula A. The present invention provides a class of linkable sialyl Lewis X analogs of structural Formula 1. These analogs have a conjugatable nucleophilic amino group, which facilitates preparation of multimeric $SLe^x$ compositions with enhanced binding properties.

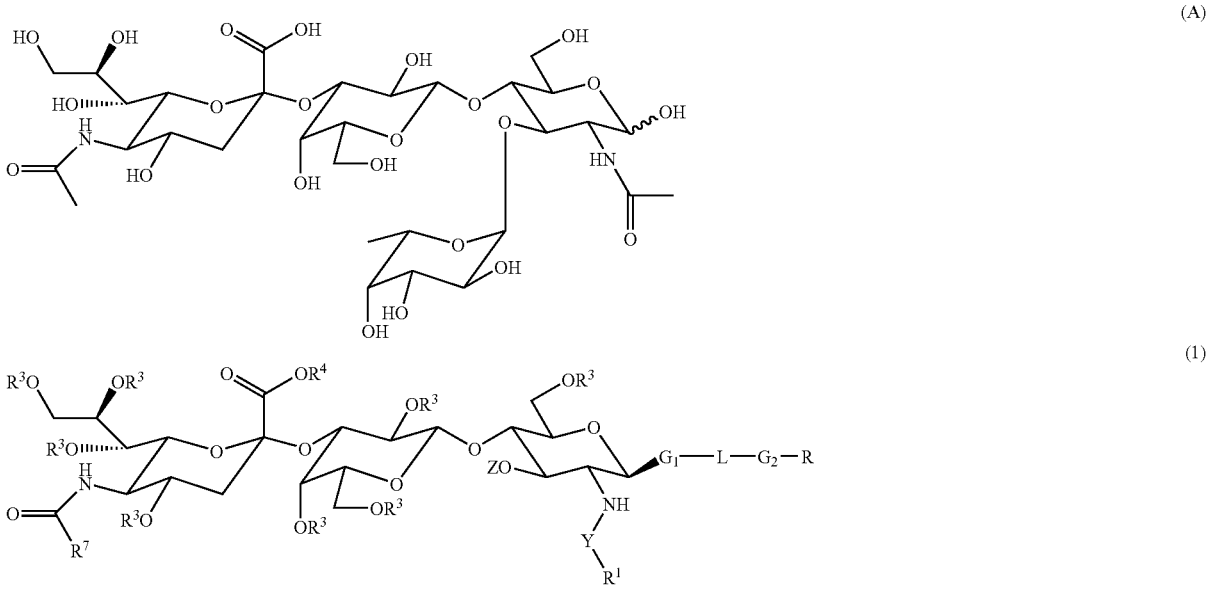

In the above structural Formula 1,

Z is hydrogen, $C_1$-$C_6$ acyl, or

Y is C(O), $SO_2$, HNC(O), OC(O), or SC(O);
$G_1$ and $G_2$ are each independently $C(R^9)_2$, $NR^{10}$, O, or S;
L is alkylidene, cycloalkylidene, arylidene, or vinylidene;
$R^2$ is hydrogen, $C(O)R^8$, $SO_2R^8$, $C(S)R^8$, $COCH_3$, or $^{14}COCH_3$;

$R_4$ is hydrogen, $C_1$-$C_6$ alkyl, aryl, arylalkyl, substituted aryl, or substituted arylalkyl;

$R^3$ and $R^5$ are each independently hydrogen, benzyl, methoxybenzyl, dimethoxybenzyl, or $C_1$-$C_6$ acyl; and $R^1$, $R^7$, $R^8$, $R^9$, and $R^{10}$ are each independently hydrogen, a $C_1$-$C_6$ alkyl, an aryl, a substituted aryl, or a phenyl $C_1$-$C_3$ alkenyl group. An aryl group has one five- or six-membered aromatic ring, fused five/six-membered aromatic rings, or two fused six-membered aromatic rings, wherein the rings are hydrocarbyl, monooxahydrocarbyl, monothiahydrocarbyl, monoazahydrocarbyl or diazahydrocarbyl rings. A substituted aryl group is an aryl group having a substituent having a halo, trifluoromethyl, nitro, $C_1$-$C_{18}$ alkyl, $C_1$-$C_{18}$ alkoxy, amino, mono-$C_1$-$C_{18}$ alkylamino, di-$C_1$-$C_{18}$ alkylamino, benzylamino, $C_1$-$C_{18}$ alkylbenzylamino, $C_1$-$C_{18}$ thioalkyl, or $C_1$-$C_{18}$ alkyl carboxamido group, or $R_1Y$ is allyloxycarbonyl or chloroacetyl.

In preferred embodiments, Y is carbonyl [C(O)], $R^1$ is hydrogen or methyl, and Z is an α-L-fucosyl whose hydroxy groups are free or blocked with a protecting group (benzyl or $C_1$-$C_6$ acyl).

In a particularly preferred embodiment of the invention, the compound is a tertrasaccharide of formula 2:

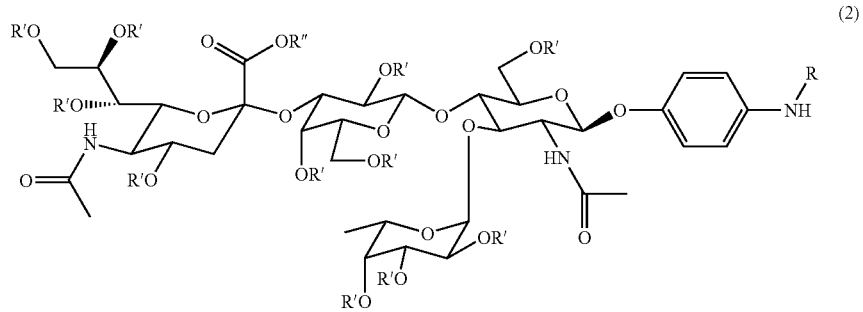

2a: R=H, R'=Ac, R"=$CH_3$; 3a: R=$COCH_3$, R'=R"=H; 3b: R=$^{14}COCH_3$, R'=R"=H wherein,
R is hydrogen, $COCH_3$ or $^{14}COCH_3$;
R' is hydrogen or acyl; and
R" is hydrogen or methyl.

In one embodiment, referred to herein as compound 2a, R is hydrogen, R' is acyl and R" is methyl. In another embodiment, R is $COCH_3$, and R' and R" are hydrogen (compound 3a). In yet another embodiment, R is $^{14}COCH_3$, and R' and R" are hydrogen (compound 3b).

The $SLe^x$ analogs of the invention may be in the form of pharmaceutically acceptable salts, which includes non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Multimeric Sialyl Lewis$^x$ Conjugates

The $SLe^x$ analog compounds of the invention can be used to target diagnostic agents or therapeutic agents, including conventional anti-inflammatory or anti-infection drugs or anti-cancer agents, to specific sites of tissue injury. By using these compounds to target a drug or diagnostic agent to a selectin receptor in vivo, higher concentrations of the drug or diagnostic agent can be achieved at the site of injury while using lower dosages. Such targeting increases the effectiveness of the drug or diagnostic agent and reduces undesirable side effects.

Targeting can be achieved by covalently attaching a selectin-binding ligand to the agent being delivered. Thus, the invention features a selectin-binding ligand conjugate that includes (1) a Sialyl $Le^x$ analog moiety, (2) a linker, and (3) a reporter moiety. The Sialyl $Le^x$ analog moiety includes one or more linkable Sialyl $Le^x$ residues, including those compounds encompassed by Formula 1 above. In a preferred embodiment, the Sialyl $Le^x$ moiety includes the residue of Formula 2a below.

The reporter moiety generally includes a diagnostic imaging agent or therapeutic agent. In one embodiment of the invention, the reporter moiety contains one or more macrocyclic or non-macrocyclic metal chelating ligand radicals that are optionally chelated to paramagnetic, super-paramagnetic, radioactive, or non-radioactive metals capable of either being detected outside the body by imaging means for diagnosis or capable of providing a therapeutic or radiotherapeutic effect. The structure of these ligands and the metals that are chelated to them may be varied depending on the desired use. Many ligands that bind to radionuclide metals are tetradentate and contain a combination of four nitrogen and/or sulfur metal coordinating atoms (i.e. $N_4$, $N_3S$, $N_2S_2$ and the like). For example, $N_4$ chelators are described in U.S. Pat. Nos. 6,143,274; 6,093,382; 5,608,110; 5,665,329; 5,656,254; and 5,688,487. Certain $N_3S$ chelators are described in PCT/CA94/00395, PCT/CA94/00479, PCT/CA95/00249 and in U.S. Pat. Nos. 5,662,885; 5,976,495; and 5,780,006. The reporter moiety may also include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in Liu and Edwards, *Chem Rev.* 1999, 99, 2235-2268 and references therein. The disclosures of each of the foregoing patents, applications and references are incorporated by reference herein, in their entirety.

The reporter moiety may also include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

Preferred metal chelating ligand radicals include those of Formula B, C, and D (for lanthamides such as paramagnetic $Gd^{3+}$ and radioactive lanthamides, such as, for example $^{177}Lu$) and those of Formula E, F, and G (for radioactive $^{99m}Tc$) set forth below. These and other metal chelating groups are described in U.S. Pat. Nos. 6,093,382 and 5,608,110, which are incorporated by reference herein in their entirety. Additionally, the chelating ligand radical of formula D is described in, for example, U.S. Pat. No. 6,143,274; the chelating ligand radical of formula F is described in, for example, U.S. Pat. Nos. 5,627,286 and 6,093,382, and the chelating ligand radical of formula G is described in, for example, U.S. Pat. Nos. 5,662,885; 5,780,006; and 5,976,495.

(2a)

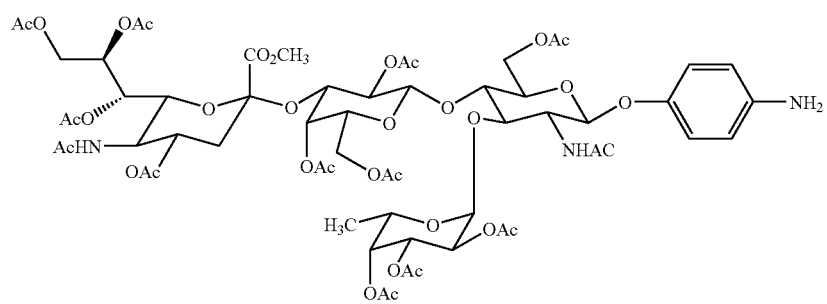

(B)

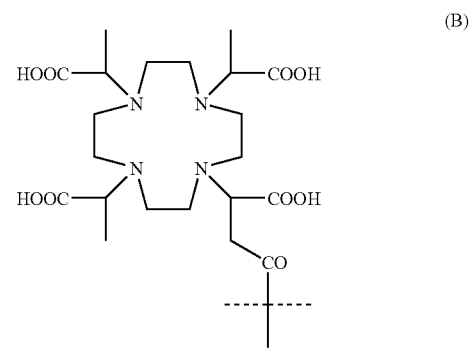

-continued (C)
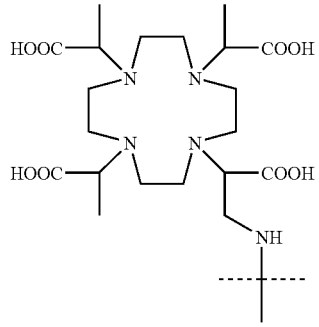

(D)
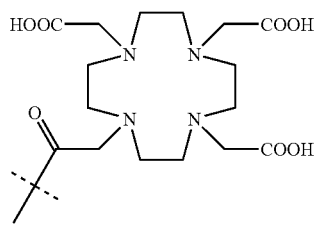

(E)
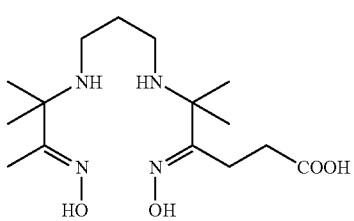

(F)
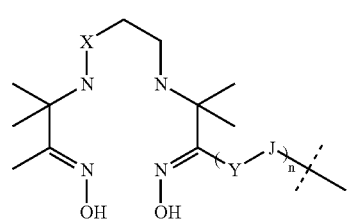

(G)
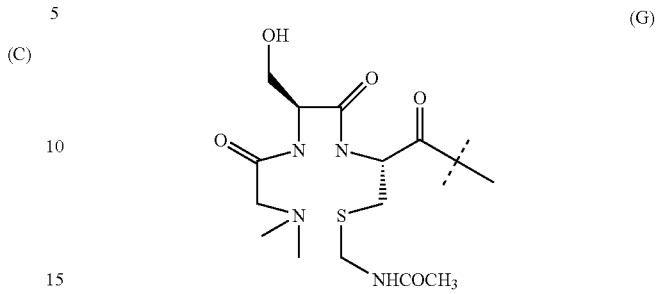

In the above Formula F, X is either CH$_2$ or O, Y is either C1-C10 branched or unbranched alkyl; Y is aryl, aryloxy, arylamino, arylaminoacyl; Y is aralkyl—where the alkyl group or groups attached to the aryl group are C1-C10 branched or unbranched alkyl groups, C1-C10 branched or unbranched hydroxy or polyhydroxyalkyl groups or polyalkoxyalkyl or polyhydroxy-polyalkoxyalkyl groups, J is C(=O)—, OC(=O)—, SO$_2$—, NC(=O)—, NC(=S)—, N(Y), NC(=NCH$_3$)—, NC(=NH)—, N=N—, homopolyamides or heteropolyamines derived from synthetic or naturally occurring amino acids; all where n is 1-100. Other variants of these structures are described, for example, in U.S. Pat. No. 6,093,382.

The metal complexes of the invention are useful as diagnostic and/or therapeutic agents. Conjugates that include paramagnetic or superparamagnetic metals are useful as diagnostic agents in MR imaging applications. Paramagnetic metals that may be used in the conjugates include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). Chromium (III), manganese (II), iron (III), and gadolinium (III).

Conjugates that include Radioactive metals are useful in radiographic imaging or radiotherapy. Preferred radio isotopes include $^{99m}$Tc, $^{51}$Cr, $^{67}$Ga, $^{68}$Ga, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au, and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In. For therapeutic purposes, the preferred radionuclides include $^{64}$Cu, $^{90}$Y, $^{105}$Rh, $^{111}$In, $^{117m}$Sn, $^{149}$Pm, $^{53}$Sm, $^{161}$Tb, $^{166}$Dy, $^{166}$Ho, $^{175}$Yb, $^{177}$Lu, $^{186/188}$Re, and $^{199}$Au.

In alternative embodiments, the reporter moiety can be a phospholipid moiety, which may be in the form of a microbubble or what has been described as a gas-filled liposome. A variety of suitable phospholipid structures are known in the art. In a preferred embodiment, the phospholipid moiety has the structure H or I shown below and described in U.S. Pat. No. 5,686,060, which is herein incorporated by reference.

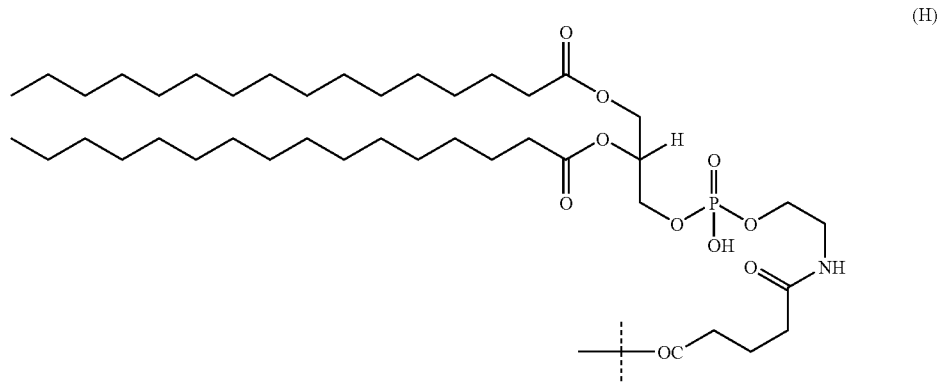

(H)

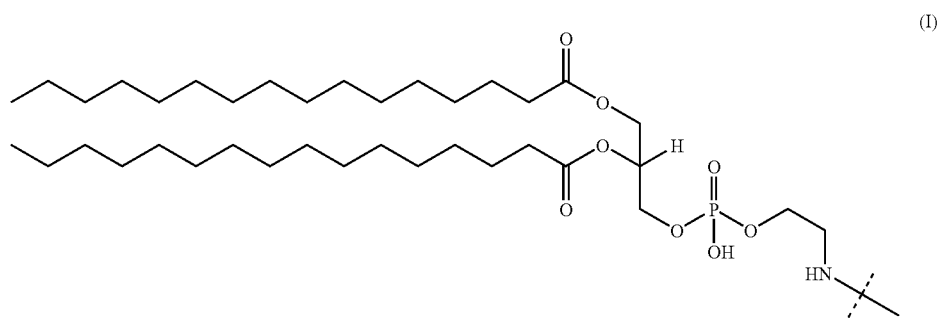

(I)

These phospholipids are incorporated into gas-filled bubbles in the presence of Disteroylphosphatidylcholine (DSPC), Dipalmitoylphosphatidylglycerol (DPPG), PEG-4000, palmitic acid and an inert gas, such as $SF_6$ or fluorocarbons like $CF_4$ and $C_4F_{10}$. Such gas-filled microbubble compositions are useful as diagnostic agents in ultrasound imaging.

In another embodiment of the invention, the reporter moiety is a cytotoxic or chemotherapeutic agent. A wide variety of chemotherapeutics can be coupled to the $SLe^x$ moiety for targeting. For example, anti-inflammatory agents that can be coupled include immunomodulators, platelet activating factor (PAF) antagonists, cyclooxygenase inhibitors, lipoxygenase inhibitors, and leukotriene antagonists. Some preferred moieties include cyclosporin A, naproxen (J), indomethacin (K), FK-506, mycophenolic acid, etc.

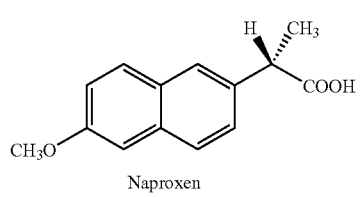

Naproxen (J)

-continued

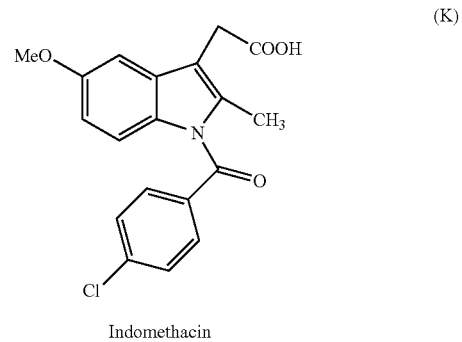

Indomethacin (K)

Similarly, antioxidants, e.g., superoxide dismutase, are useful in treating reperfusion injury when targeted by a contemplated saccharide compound. Likewise, the $SLe^x$ moiety can be coupled to anti-cancer agents, such as derivatized paclitaxel (TAXOL (L)), docetaxel, vinca alkaloids such as vincristine, vinblastine, dolostatins, daunomycin, doxorubicin, bleomycin, halichondrins, etc.

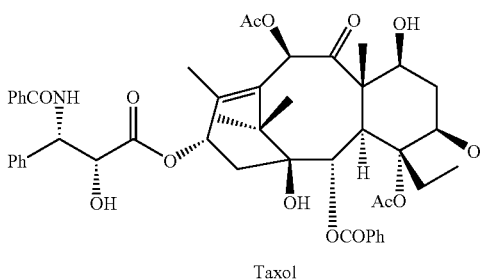

Taxol

Similarly, for the purpose of a dual mode therapy of infection, the SLe$^x$ moiety can be coupled to antibiotics, such as quinolone, antibiotics, penicillin, cephalosporins, such as Cefuroxime (M), oxazolidinones, such as Linezolid (N), cyclosporin, Vancomycin or more generally either Gram positive or Gram negative or broad spectrum antibiotics, through suitable functionality, thus allowing directed release of the antibiotic and also inhibition of cellular adhesion of pathogen. Examples of other suitable chemotherapeutic agents are described in U.S. Pat. No. 6,093,382.

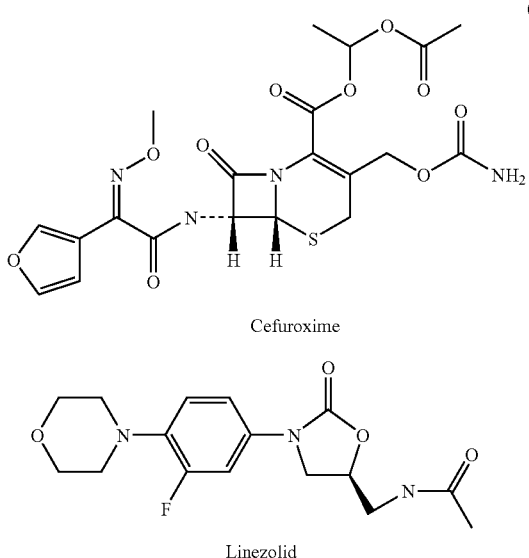

Cefuroxime

Linezolid

A general principle for conjugation of drugs or other bioactive molecules is that the site of conjugation should be one where there exists capability for in vivo cleavage by endogenous amidases, proteases, esterases or other enzymes such as endonucleases, and phosphatases for example. Such strategies employing more active carboxyesters, phosphate esters or easily cleaved carboxamides or sulfonamides are known in the use of prodrugs that depend on these forms of metabolic activation or release. Similarly useful are release systems dependant on enzymatically mediated oxidative or reductive bioactivation/release.

The selectin receptor targeting can also be accomplished via amphipaths, or dual character molecules (polar:nonpolar) that exist as aggregates in aqueous solution. Amphipaths include nonpolar lipids, polar lipids, mono- and diglycerides, sulfatides, lysolecithin, phospholipids, sapchin, bile acids, and salts. These molecules can exist as emulsions and foams, micelles, insoluble monolayers, liquid crystals, phospholipid dispersions and lamellar layers (collectively referred to herein as liposomes), and can be used to deliver therapeutic or diagnostic agents. In these preparations the drug or diagnostic agent to be delivered is incorporated as part of a liquid-filled liposome in conjunction with a SLe$^x$ analog compound that binds to the selectin receptor. Thus, liposomes filled with a desired agent can be directed to a site of tissue injury by the selectin-SLe$^x$ analogue compound interaction. When the liposomes are brought into the proximity of the affected cells, they may deliver the selected therapeutic or diagnostic compositions by passive diffusion, active diffusion or by any endogenous or exogenous process which serves to facilitate delivery to the required site of action. This includes any process or technique of irradiation employed to disrupt the liposome at the target, such as enzymatic degradation, thermal stimulation, physical manipulation or vibration, any form of ultrasound provoked disruption of the liposome at the target area. The preparation of suitable liposomes and methods for coupling them to targeting agents are known in the art and are described, for example, in U.S. Pat. Nos. 4,957,773, 4,603,044, 4,501,728, 4,037,028 and 4,235,871 each of which is herein incorporated by reference.

The selectin binding moiety (i.e., the SLe$^x$ residue) can be directly or indirectly bound to the reporter moiety. The coupling, which can be performed by a variety of well known methods, should not inhibit the ability of the selectin-binding ligand to bind to the receptor, nor should it substantially reduce the activity or function of the reporter moiety. This may be accomplished by using a variety of linkers known in the art. The linker can be any chemical moiety which serves to covalently bind the reporter to the SLe$^x$ moiety. The linker should physically separate, or otherwise isolate the reporter moiety from the selectin binding moiety. In a preferred embodiment, the linker residue attaching the Sialyl Le$^x$ moiety and the reporter moiety has the structure depicted in formula O:

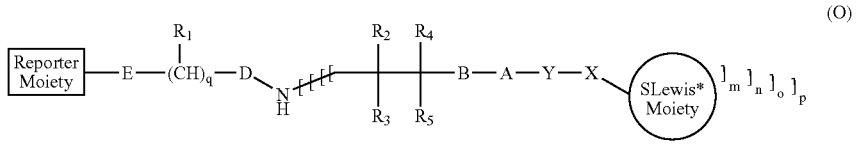

wherein,
- X is O, S, or $[CH(R_1)]_z$—$[N(R_6)]_w$—where z is not 1, but can be 0, or 2 to 10, and w is 0 to 1
- Y is alkylidene, cycloalkylidene, arylidene, or vinylidene;
- A is —C(=O)—, —(C=S)—, or —$[CH(R_1)]_t$—$[N(R_6)]_w$—where t is 0 to 10 and w is 0 to 1;
- B is O, S, or N(R') when A is —C(=O)— or —(C=S)—, or is —C(=O)— or —(C=S)— when A is —$[CH(R_1)]_t$—$[N(R_6)]_w$—where t is 0 to 10 and w is 0 to 1;
- D is —C(=O)—, —(C=S)—, or —$[CH(R_1)]_z$—$[N(R_6)]_w$—where z is not 1, but can be 0, or 2 to 10 and w is 0 to 1
- E is —C(=O)—, —(C=S)—, or —$[CH(R_1)]_u$—$[N(R_6)]_w$—where u is 0 to 10 and w is 0 to 1;
- q is 0 to 10 when D is —C(=O)— or —(C=S)—, or is 2 to 10 when D is —$[CH(R_1)]_z$—$[N(R_6)]_w$— and z is 0 and w is 0 to 1, or is 0 to 10 when D is —$[CH(R_1)]_z$—$[N(R_6)]_w$— and z is 2 to 10 and w is 0 to 1;
- m, n, o, and p are independently 1 to 3; and
- $R_1$, $R_2$, $R_3$, $R_4$, $R_5$, $R_6$ are independently alkyl, hydroxyalkyl, alkoxy, alkoxyalkyl, cycloalkyl, cycloalkoxy, aryl, or aryloxy.

The construction of such linker moieties and their conjugation to both reporters and targeting vectors is well known and described in U.S. Pat. No. 6,093,382, which is wholly incorporated by reference herein. Additional methods for construction of desired multimeric assemblies having multiple targeting and/or reporter moieties, wherein the distances between the targeting functions and the reporter functions, between multiple targeting functions, and/or between multiple reporter functions can be controlled, are known in the art.

The employment of multimeric peptidic core scaffolds for construction of multimeric structures (Veprek, P. and Jezek, J (1999) J. Peptide Sci. 5, 5) is easily accomplished by either solution or solid phase synthesis techniques which may employ orthogonal or quasiorthogonal protecting group strategies. Similarly such protecting group strategies allow controlled introduction of reporters and targeting ligands. Modulation of the distance between the core termini of multimeric structures bearing the targeting functions and reporters using oligomeric amide based linker chemistry is known in the art (Rose, K. and Vizzavona, J. (1999) J. Am. Chem. Soc. 121, 7034, Roy R, Zanini, D. Meunier, S. J and Romanowska, A. (1993) J. Chem. Soc. Chem. Commun. 1869) and results in the ability to tune the affinity of the system for the target (Glick, G. D. and Knowles, J. R. (1991) J. Am. Chem. Soc. 113, 4701.). The references cited herein are incorporated by reference in their entirety.

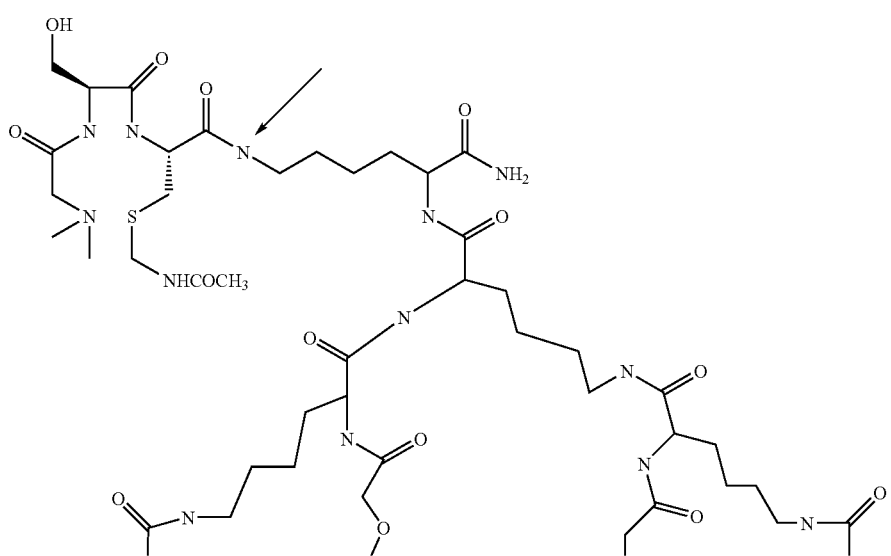

(P)

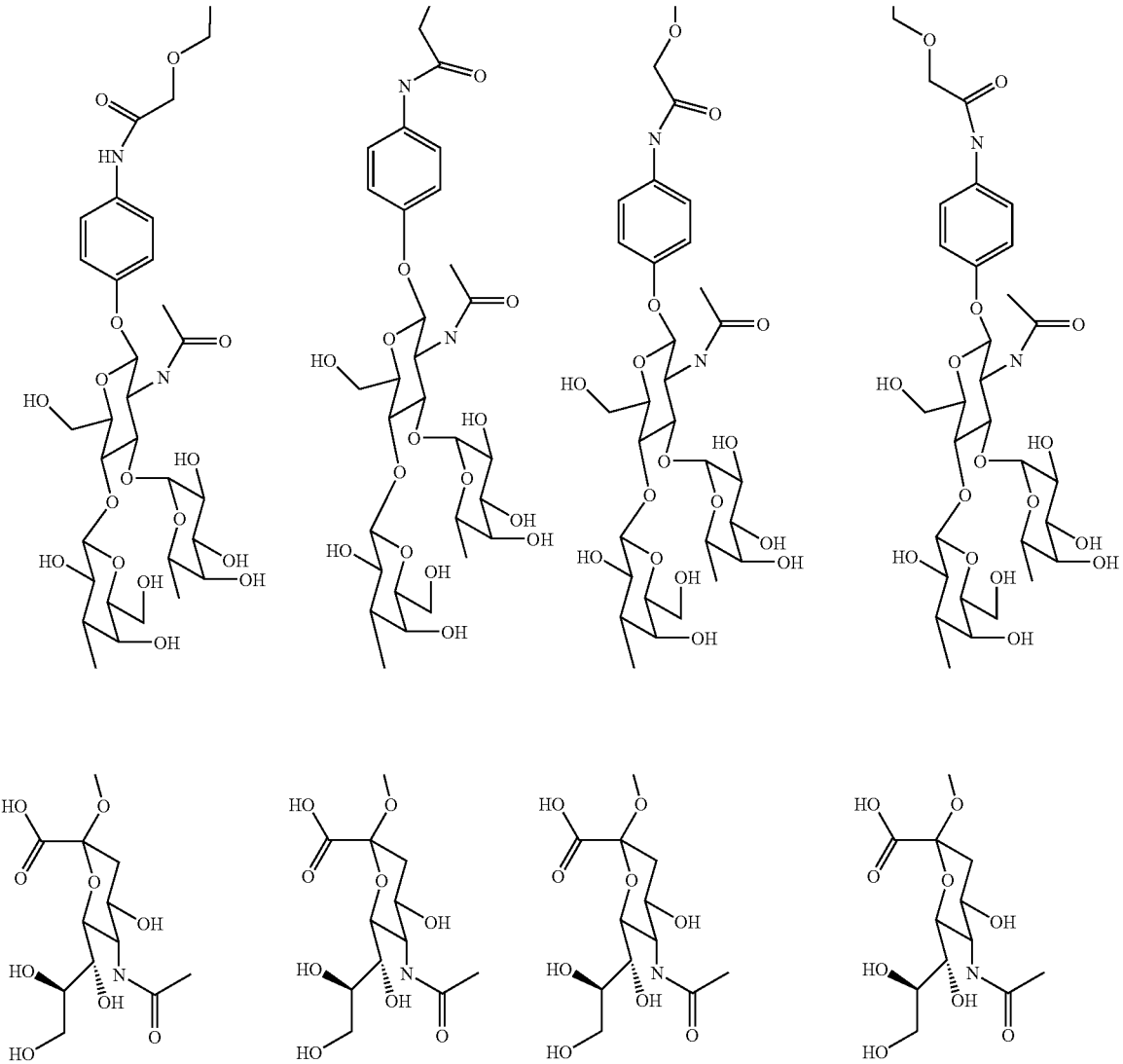

The structure P composed of a trilysine branched peptidic core, the glycolic acid spacers, and the reporter ligand radical G, (which is employed to chelate the radiosotope $^{99m}$Tc for radioimaging) conjugated to a Sialyl Le$^x$ analog moiety including four Sialyl Le$^x$ derivatives can be produced using the methods and systems described above. This material, when chelated with $^{99m}$Tc is useful for imaging sites of inflammation and infection. Reporter groups of other kinds can be conjugated to this Sialyl Le$^x$ analog moiety by preparation of appropriate activated derivatives such as mixed carbamates (where the reporter has an amino group available) or mixed carbonic esters (where the reporter has a hydroxyl group available) that can react at the epsilon amino group of the root lysine (indicated by the arrow) of structure P. Similarly any group capable of direct reaction or reaction after suitable activation, with the lysine epsilon amino group, if present in a reporter function, a chemotherapeutic, an anti-inflammatory as described earlier, can be employed to prepare derivatives bearing the Sialyl Le$^x$ analog moiety shown in structure P. Alternatively, the epsilon amino group of the core lysine of the Sialyl Le$^x$ analog moiety can be converted to a reactive carbamate, or isocyanate, or isothiocyante by treatment with bis-p-nitrophenylcarbonate, phosgene or equivalents known in the art, or thiocarbonyl chloride respectively. These reactive electrophiles can be employed for functionalization of reporters bearing amino groups, and this encompasses reporters functionalized with spacers or linkers that bear amino groups capable of reacting with the electrophiles described above.

The application of the methods described also allows the preparation of constructs bearing multiple reporters and multiple SLe$^x$ residues in the same molecule. Such systems are exemplified by the compound (Q) useful for radioimaging when the macrocycles are employed for chelation of radiometals such as $^{111}$In or for MRI imaging when, for example, the macrocycles are employed for the chelation of nonradioactive isotopes of gadolinium.

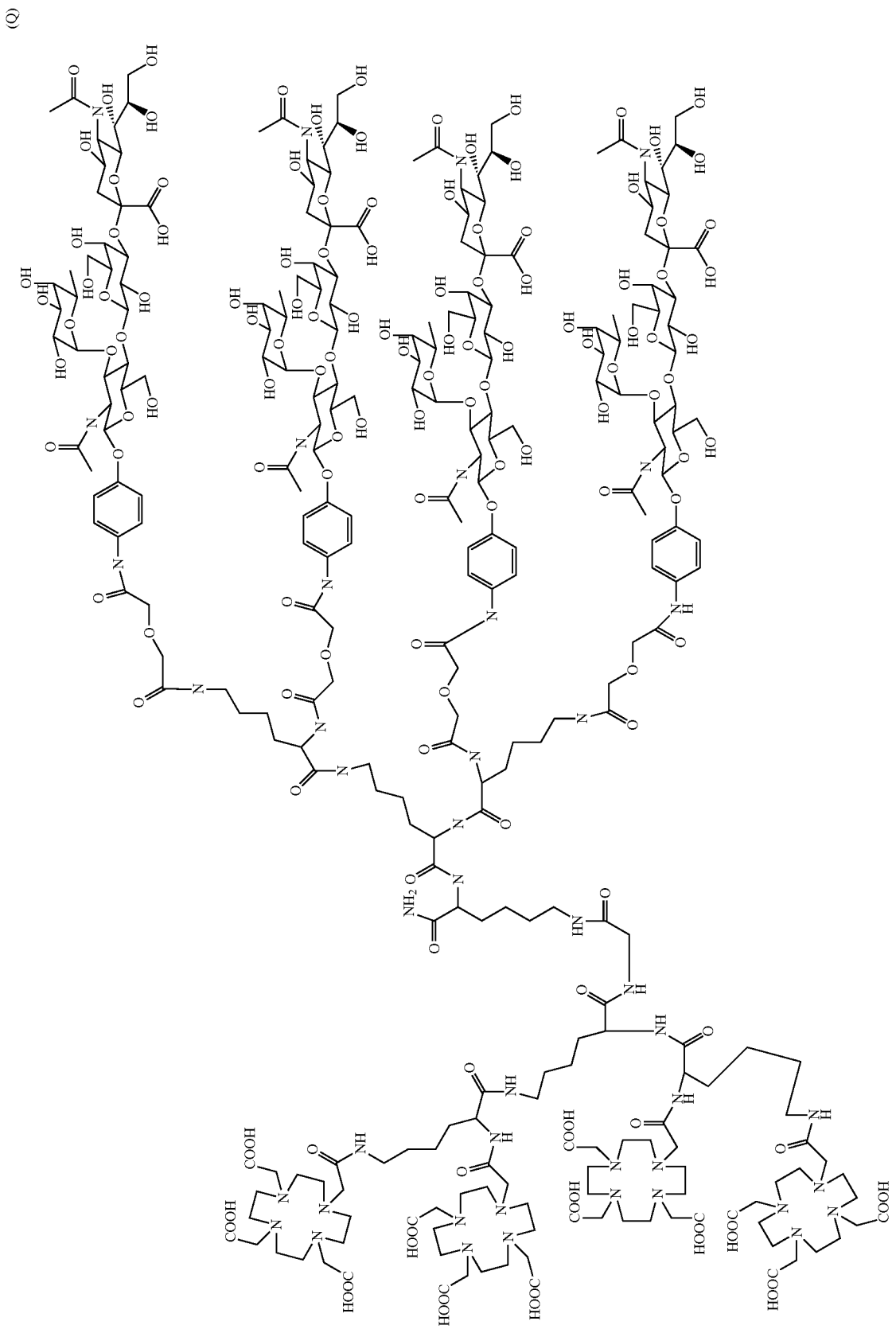

Characteristics of the Position of Conjugation of Chemotherapeutics that are Expected to Remain Bound to the Targeting Construct Where it is expected that a cytotoxic or chemotherapeutic drug should remain attached to the construct while performing the function for which it was incorporated, a general principal is that the site of attachment of the drug should be planned based on prior QSAR (quantitative structure-activity relationship) that indicates that substituents at that site have as small as possible a deleterious effect on the activity of the drug. Such principles are well established in the synthesis of conjugates of drugs employed for fluorescence polarization assays for drugs of abuse, for example.

Cell Adhesion Inhibition Assay Methods

Numerous direct and indirect methods for in vitro screening of inhibitors of ligand-receptor interactions are available and known to those skilled in the art, and can be used to determine whether a particular compound has the ability to inhibit the adhesion of $SLe^x$-bearing cells to cells expressing a particular selectin.

Several selectin receptor genes have been cloned, and thus, the genes can be inserted and expressed in a wide variety of cells, such as COS cells, CHO cells, adenovirus-transformed human kidney cells, and the like, so that a recombinant selectin receptor such as rELAM (recombinant ELAM-1) can be used in the assays. In addition, cells that do not normally express $SLe^x$ are capable of being transformed with one or more glycosyltransferase genes that confer on the transformed cells the ability to synthesize the ligand. (See, e.g., Lowe et al., Cell, 63:475-484 (1990)). In some assays, the inhibitor compound or agent is incubated with labeled $SLe^x$-bearing cells and activated cells expressing cell surface selectins or recombinant selectin immobilized on a solid surface. Inhibition of cellular adhesion can then be determined by detecting label bound to the surface after appropriate washes.

Typically, the in vitro assays of a contemplated $SLe^x$ analog compound are competition assays that detect the ability of a contemplated compound to competitively inhibit binding of selectin to cells containing $SLe^x$. Selectin-containing cells are typically activated platelets or activated endothelial cells with a recombinant selectin being as useful. The $SLe^x$-bearing cells are usually neutrophils or HL-60 cells.

Other assay formats involve detection of the presence or absence of various physiological changes in either $SLe^x$ ligand-bearing or selectin-bearing cells that result from the interaction. Examples of suitable assays include the measurement of changes in transcription activity induced by binding (see, e.g., PCT Publication No. 3712820), the detection of various cell mediated extra-cellular effects (see, e.g., PCT Publication No. 90/00503), and the detection of changes in the membrane potential of individual cells (see, e.g., U.S. Pat. No. 4,343,782), all of which are incorporated herein by reference. Alternatively, conformational changes in isolated receptors or ligands can be detected (see, e.g., U.S. Pat. No. 4,859,609), which is incorporated herein by reference. Still further, one can bind $SLe^x$-expressing cells to solid support-bound selectin, lyse the bound cells and assay for a protein that could only have been present in the bound cells.

Any component of the assay, including the ligand, the selectin receptor, or the $SLe^x$ compound, can be bound to a solid surface, such as a membrane (e.g., nitrocellulose), a microtiter dish (e.g., PVC or polystyrene) or a bead. Many methods for immobilizing biomolecules on solid surfaces are known in the art. The desired component can be covalently bound or non-covalently attached to the surface. The manner of linking a wide variety of compounds to various surfaces is well known and is amply illustrated in the literature. See for example Immobilized Enzymes, Inchiro Chibata, Halsted Press, New York (1978), Cuatrecasas, *J. Biol. Chem.*, 245: 3059 (1970), and U.S. Pat. Nos. 4,447,576 and 4,254,082, which are incorporated herein by reference.

A wide variety of organic and inorganic polymers, both natural and synthetic, can be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), silicones, polyformaldehyde, cellulose, cellulose acetate, nitrocellulose, etc. Other materials that can be employed include paper, glasses, ceramics, metals, metalloids, semiconductive materials, cermets or the like. In addition are included substances that form gels, such as proteins, e.g., gelatins, lipopolysaccharides, silicates, agarose and polyacrylamides or polymers which form several aqueous phases, such as dextrans, polyalkylene glycols (alkylene of 2 to 3 carbon atoms) or surfactants, e.g., amphiphilic compounds, such as phospholipids, long chain (12-24 carbon atoms) alkyl ammonium salts and the like. Where the solid surface is porous, various pore sizes may be employed depending upon the nature of the system.

The label used in this assay can be coupled directly or indirectly to the desired assay component according to methods well known in the art, or can be a protein endogenous to the bound cells. A wide variety of labels can be used, and the assay component can be labeled by any one of several methods. The choice of label depends on sensitivity required, ease of conjugation with the compound, stability requirements, and available instrumentation. The most common method of detection is the use of autoradiography with $^3H$, $^{125}I$, $^{35}S$, $^{14}C$, or $^{32}P$ labeled compounds or the like. The choice of radioactive isotope depends on research preferences due to ease of synthesis, varying stability, and half lives of the selected isotopes. Other non-radioactive labels include ligands which bind to labeled antibodies, fluorophores, chemiluminescent agents, enzymes, and antibodies which can serve as specific binding pair members for a labeled ligand.

Suitable fluorescent labels include fluorescein and its derivatives, rhodamine and its derivatives, dansyl, umbelliferone, etc. Chemiluminescent compounds include luciferin, and 2,3-dihydrophthalazinediones, e.g., luminol. Enzymes of interest as labels are primarily hydrolases, particularly phosphatases, esterases and glycosidases, or oxidoreductases, particularly peroxidases. The label can also be an enzyme or other protein present in a cell whose adhesion is to be inhibited. The amount of that enzyme can thereby be used as a label to determine the amount of binding. Myeloperoxidase is one such protein present in HL-60 cells that is useful as a label in the binding inhibition studies discussed hereinafter. For a review of various signal producing systems which may be used, see, U.S. Pat. No. 4,391,904, which is incorporated herein by reference.

Pharmaceutical Compositions

The invention also provides pharmaceutical compositions that include a therapeutically effective amount of a contemplated $SLe^x$ analog or conjugate compound, or a pharmaceutically acceptable salt thereof, dissolved or dispersed in a pharmaceutically acceptable carrier or diluent adapted for the route of administration. As will be seen from the following disclosure, a therapeutically effective amount can vary widely. When used to treat inflammatory related diseases, the amount is preferably sufficient to inhibit binding of sialyl $Le^x$ to cells bearing selectin on their surfaces, preferably by about one-half or more. An exemplary cellular adhesion-inhibiting amount is about 5 to about 60 mg/kg.

The compositions of the invention can be administered orally, parenterally (e.g. intramuscular, intraperitoneal, intravenous or subcutaneous injection, or implant), nasally, vaginally, rectally, sublingually, or topically. Methods well known in the art for making formulations are found, for example, in *Remington's Pharmaceutical Sciences* (18$^{th}$ edition), ed. A. Gennaro, 1990, Mack Publishing Company, Easton, Pa. and in Langer, *Science*, 249:1527-1533 (1990). Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, glucose, mannitol, cellulose, starch, calcium phosphate, sodium phosphate, kaolin and the like. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Preferably, the pharmaceutical compositions are administered intravenously. Formulations for parenteral administration include sterile aqueous or non-aqueous solutions, suspensions, or emulsions. A variety of aqueous carriers can be used, e.g., water, buffered water, 0.4 percent saline, and the like. Examples of other suitable vehicles include propylene glycol, polyethylene glycol, vegetable oils, gelatin, hydrogenated naphalenes, and injectable organic esters, such as ethyl oleate. Such formulations may also contain auxiliary substances, such as preserving, wetting, buffering, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the compounds of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

The concentration of SLe$^x$ analog compound utilized in the liquid formulations is usually at least about 1 percent to as much as 10 to 30 percent by weight and is selected primarily by fluid volumes, viscosities, etc., in accordance with the particular mode of administration selected. For oral administration, the concentration is generally 10-95 percent of active ingredient (i.e., SLe$^x$ analog compound), preferably about 20 percent (see, Remington's, supra).

For aerosol administration, a contemplated SLe$^x$ analog compound is preferably supplied in finely divided form along with a surfactant and propellant. Typical percentages of a SLe$^x$ analog compound are about 0.5 to about 30 percent by weight, and preferably about 1 to about 10 percent. The surfactant must of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides can be employed. The surfactant can constitute about 0.1 to about 20 percent by weight of the composition, and preferably about 0.25 to about 5 percent. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve.

As discussed above, the amount of active ingredient in the compositions of the invention can be varied. One skilled in the art will appreciate that the exact individual dosages may be adjusted somewhat depending upon a variety of factors, including the specific SLe$^x$ compound being administered, the time of administration, the route of administration, the nature of the formulation, the rate of excretion, the particular disease being treated and its severity, and the age, weight, health, and gender of the patient Generally, dosage levels of between 10 μg/kg to 100 mg/kg of body weight are administered daily as a single dose or divided into multiple doses. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

The SLe$^x$ compounds can be administered in a sustained release composition, such as those described in, for example, U.S. Pat. Nos. 5,672,659 and 5,595,760. The use of immediate or sustained release compositions depends on the type of condition being treated. If the condition consists of an acute or over-acute disorder, a treatment with an immediate release form will be preferred over a prolonged release composition. Alternatively, for preventative or long-term treatments, a sustained released composition will generally be preferred.

The pharmaceutical compositions of the invention can be used to block or inhibit cellular adhesion associated with a variety of disorders. For instance, a number of inflammatory disorders are associated with selectins expressed on vascular endothelial cells and platelets. The inflammatory response to be treated may be a reaction to either the specific or non-specific defense systems or both. Examples of specific defense system reactions include antibody response to antigens, such as viruses, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of peripheral mononuclear (PMN) leukocytes at sites of bacterial infection (e.g., pulmonary infiltrates in bacterial pneumonia and pus formation in abscesses).

Other treatable disorders include, e.g., rheumatoid arthritis, post-ischemic leukocyte-mediated tissue damage (reperfusion injury), frost-bite injury or shock, acute leukocyte-mediated lung injury (e.g., adult respiratory distress syndrome), asthma, infection, thrombotic disorders (e.g., stroke, myocardial infarctions, deep vein thrombosis, pulmonary embolism, etc.), traumatic shock, septic shock, nephritis, and acute and chronic inflammation, including atopic dermatitis, psoriasis, and inflammatory bowel disease. Various platelet-mediated pathologies such as atherosclerosis and clotting can also be treated. In addition, tumor metastasis can be inhibited or prevented by inhibiting the adhesion of circulating cancer cells. Examples include melanoma and carcinoma of the colon In light of the complexity of the inflammatory response in mammals, one of skill in the art will readily recognize that a contemplated pharmaceutical composition can further include other compounds known to interfere with the function of other cellular adhesion molecules. For instance, members of the integrin family of adhesion molecules are thought to play a role in the extravasation of leukocytes at points of infection. For a review of intercellular adhesion receptors, including selectin receptors, and their role immune function, see Springer, Nature, 346:425-434 (1990). In addition, successful treatment using a contemplated pharmaceutical composition can also be determined by the state of development of the condition to be treated. Because different adhesion molecules can be up or down regulated in response to a variety of factors during the course of the disease or condition, one of skill will recognize that different pharmaceutical compositions can be required for treatment of different inflammatory states.

A pharmaceutical composition containing a SLe$^x$ analog compound can be administered for prophylactic and/or therapeutic treatments. In therapeutic applications, a composition is administered to a patient already suffering from a disease, as described above, in an amount sufficient to inhibit binding between cells expressing a selectin and cells bearing SLe$^X$ on their surfaces (i.e., an amount sufficient to cure or at least partially arrest the symptoms of the disease and its complications). As mentioned above, the exact amounts effective for this use depend, inter alia, on the severity of the disease and the weight and general state of the patient, but generally range from about 0.5 mg to about 10,000 mg of SLe$^x$ analog compound per day for a 70 kg patient, with dosages of from about 5 mg to about 2,000 mg of a compound per day being more commonly used.

In prophylactic applications, a composition containing a contemplated compound is administered to a patient susceptible to or otherwise at risk of a particular disease. In this use, the precise amounts again depend on the patient's state of health and weight, but generally range from about 0.5 mg to about 5,000 mg per 70 kilogram patient, more commonly from about 5 mg to about 2,000 mg per 70 kg of body weight.

Another way to assess an adhesion-inhibiting amount of a contemplated SLe$^x$ analogue or conjugate compound is to compare its binding strength to that provided by SLe$^x$ itself. One convenient way to make that comparison is by use of the $IC_{50}$ (the concentration needed to inhibit binding by one-half) of the two compared materials, and base the amount used on the amount of SLe$^x$ and an amount of the SLe$^x$ analog compound that is a multiple of the $IC_{50}$ value for that compound.

Single or multiple administrations of a composition can be carried out with dose levels and pattern being selected by the treating physician. In any event, the pharmaceutical formulations should provide a quantity of a SLe$^x$ analogue or conjugate compound sufficient to effectively treat the patient.

The compounds of the invention can also find use as diagnostic agents. For example, labeled compounds can be used to locate areas of inflammation or tumor metastasis in a patient suspected of having an inflammation. For this use, the compounds can be labeled with $^{125}I$, $^{14}C$, or tritium. Alternatively, as discussed above, the SLe$^x$ conjugate compounds of the invention may be linked to a reporter moiety that includes a diagnostic agent useful for MRI, ultrasound, or radiodiagnostic techniques. Doses for administration of paramagnetic metal complexes for MR imaging range from about 0.05 to about 0.3 mmol/kg of body weight. For radiopharmaceutical compositions, the amount administered may be selected based on the desired use, such as to produce a diagnostic image of an organ, by methods known in the art. Doses may range from about 2 to 200 mCi, or as limited by in vivo dosimetry provided by the radiopharmaceutical.

Synthesis of Compounds

The SLe$^x$ analogs of the invention can be prepared in numerous ways. A representative synthesis is outlined in reaction schemes 1-9 provided in the Example section below. Although this outline describes the preparation of SLe$^x$ analog 4-(acetamido)phenyl(methyl 5-acetamido-3,5-dideoxy-α-D-glycero-D-galacto-2-nonulopyranuronate)-(2→3)-O-(α-D-galactopyranosyl)-(1→4)-O-(α-L-fucopyranosyl-(1→3))-2-deoxy-2-(acetamido)-β-D-glucopyranoside, use of appropriate alternative starting materials will yield other analogs of the invention. Thus, the synthesis described herein is general in nature.

The synthesis of the tetrasaccharide of Formula 2a involves two basic steps. First, the four individual protected monosaccharides subunits (the glucosmainyl, fucosyl, galactosyl, and sialyl residues) are synthesized. The monomers are then coupled to obtain the final tetrasaccharide compound. The four monomeric units are preferably coupled using a 3+1 strategy, wherein the glucosmainyl, fucosyl and galactosyl residues are first assembled and then joined to sialyl residue. Alternatively, a 2+2 strategy may be used, which involves preparing the protected fucosyl-glucoside and sialyl-galactoside and then coupling these two disaccharides together.

The present invention is illustrated by the following examples, which describe the synthesis and binding properties of SLe$^x$ analogs. These examples are in no way intended to be limiting of the invention.

Outline of Synthesis of Sialyl Lewis X Analog 4-(acetamido)phenyl(methyl 5-acetamido-3,5-dideoxy-α-D-glycero-D-galacto-2-nonulopyranuronate)-(2→3)-O-(β-D-galactopyranosyl)-(1→4)-O-(α-L-fucopyranosyl-(1→3))-2-deoxy-2-(acetamido)-β-D-glucopyranoside a. The Synthesis of the Four Protected Monosaccharide Units i) Synthesis of 4-nitrophenyl 2-acetamido-4,6-benzylidine 2-deoxy-β-D-glucopyranoside (Compound 5).

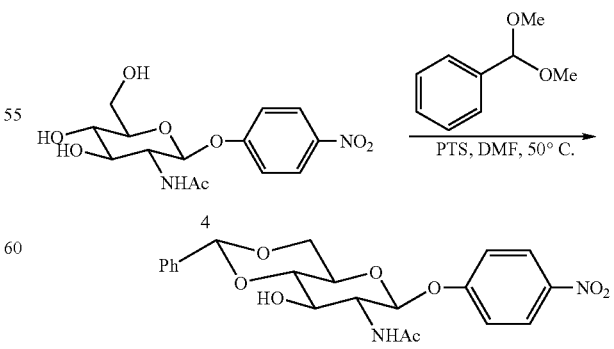

As shown in Scheme 1, the benzylidene protection of (4-nitrophenyl) 2-acetamido-2-deoxy-β-D-glucopyranoside (compound 4) was effected by treatment with benzaldehyde dimethylacetal under catalysis with PTS in DMF in 97% yield (see Example 2) to obtain 4-nitrophenyl 2-acetamido-4,6-benzylidine 2-deoxy-β-D-glucopyranoside (compound 5), which serves as the glycosyl acceptor in the coupling reaction with the fucosyl donor (compound 9).

ii) Synthesis of 2,3,4-tri-O-benzyl-α-L-fucopyranosyl Bromide (Compound 9)

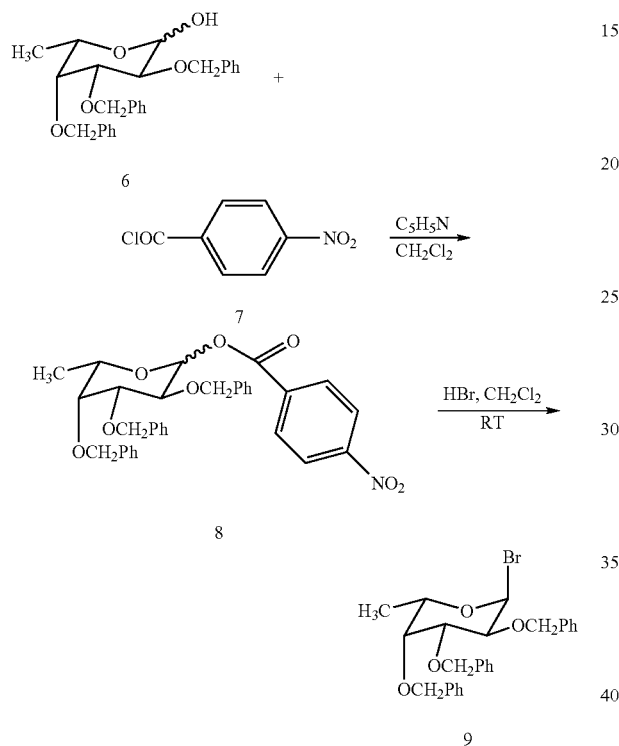

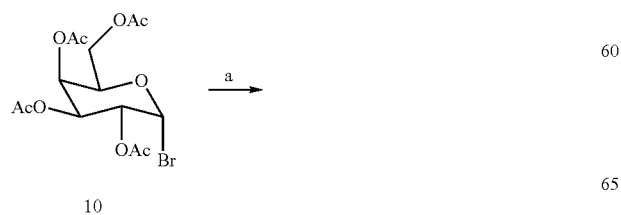

Scheme 2 shows the preparation of the fucosyl donor (compound 9). 2,3,4-Tri-O-benzyl-L-fucopyranose (compound 6) was treated with 4-nitrobenzoyl chloride (compound 7) in the presence of pyridine in $CH_2Cl_2$ to obtain the intermediate (compound 8) as a mixture of the α and β epimers in 80% yield. Bromination of the mixture 8 with HBr in $CH_2Cl_2$ afforded solely the fucosyl α-bromide β in 95% yield. This bromide was unstable and it was used as such immediately in the next step.

iii) Synthesis of 2,3,4-tri-O-acetyl-6-O-benzyl-α-D-galactopyranosyl Trichloroacetimidate (Compound 15)

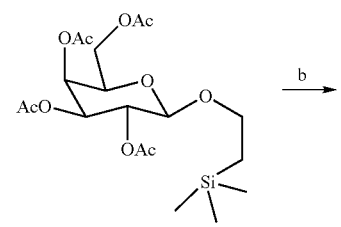

11

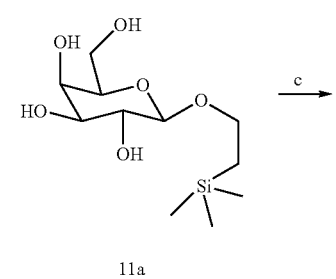

11a

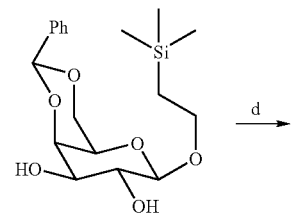

12

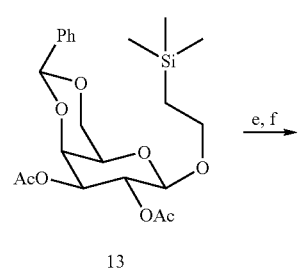

13

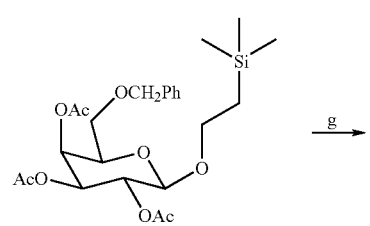

14

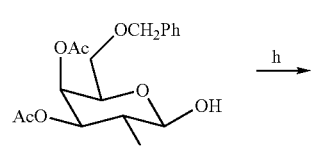

14a

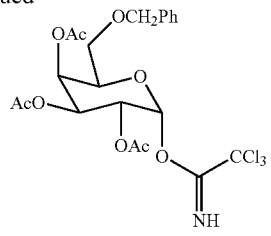

15

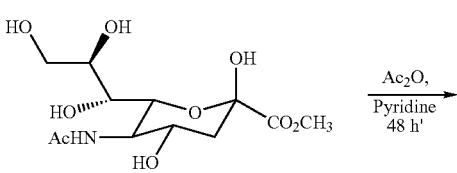

17

In scheme 3, the following reagents were used:
a) $(CH_3)_3SiCH_2CH_2OH$, HgO, $HgBr_2$, $CH_2Cl_2$;
b) NaOMe, MeOH;
c) $PhCH(OCH_3)_2$, PTS, DMF;
d) $Ac_2O$, $N(Et)_3$, $CH_2Cl_2$;
e) $BH_3 \cdot NMe_3$, $AlCl_3$, THF, Molecular sieve 4 Å;
f) $Ac_2O$, $N(Et)_3$, $CH_2Cl_2$;
g) TFA, $CH_2Cl_2$; and
h) $CCl_3CN$, DBU, $CH_2Cl_2$.

Scheme 3 shows the preparation of the galactopyranosyl donor (compound 14). First, 2,3,4,6-Tetra-O-acetyl-α-D-galactopyranosyl bromide (compound 10) was reacted with 1-(trimethylsilyl)ethanol in $CH_2Cl_2$ in the presence of $CaSO_4$, HgO, and $HgBr_2$ to obtain the galactoside 11 in 74% yield. Deacetylation with sodium methoxide in methanol, followed by benezylidination in the presence of PTS in DMF furnished the protected diol 12 in 84% yield. Acetylation of the diol 12 with $AC_2O$ in the presence of $NEt_3$ afforded the diacetate 13 in 82% yield. Cleavage of the ketal ring of compound 13, with simultaneous reduction of the intermediate hemiacetal, by treatment with $BH_3$—$NMe_3$ in the presence of $AlCl_3$ in THF followed by acetylation with $AC_2O$ in pyridine gave the orthogonally protected galactoside compound 14 in 49% yield. Solvolysis of compound 14 with TFA and subsequent reaction with $CCl_3CN$ in the presence of DBU in $CH_2Cl_2$ afforded 2,3,4-tri-O-acetyl-6-O-benzyl-α-D-galactopyranosyl trichloroacetimidate (compound 15) in 75% yield. Proton NMR signal of 15 at δ 6.58 (d,$j_{1,2}$=3.5$H_2$H-1 and δ 8.63 (C=NH) confirmed the anomeric configuration of compound 15 to be α.

iv) Methyl 5-acetamido-4,7,8,9-tetra-O-acetyl-3,5-dideoxy-S-phenyl-2-thio-D-glycero-D-galacto-2-nonulopyronosuronate (Compound 19)

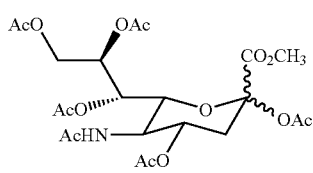

18

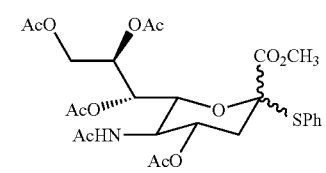

19

Scheme 4 illustrates the preparation of the phenylthio monosaccharide 19 based on the sialic acid moiety. 5-Acetamido-3,5-dideoxy-D-glycero-D-galacto-2-nonulopyronosuronic acid (compound 16) was converted into the corresponding methyl ester compound 17 by treatment with MeOH in the presence of Dowex-50-$H^+$ in 98% yield. Conversion of the ester (compound 17) into the phenylthio glycoside (compound 19) was achieved as described by Sharma and Eby, *Carbohydrate Res.*, 127:201-210 (1984). Per-acetylation of compound 17 with $Ac_2O$ in pyridine furnished the acetylated methyl ester 18 in 89% yield as a mixture (3.3/1.0) of anomers, based on its NMR spectrum. Treatment of compound 18 with thiophenol in the presence of $BF_3 \cdot Et_2O$ in $CH_2Cl_2$ afforded methyl 5-acetamido-4,7,8,9-tetra-O-acetyl-3,5-dideoxy-S-phenyl-2-thio-D-glycero-D-galacto-2-nonulopyronosuronate (compound 19) in 92% yield as a mixture (80/20) of anomers.

b. Coupling of the Protected Monomers to Obtain the Conjugatable Aminophenyl Tetrasaccharide (Compound 2a)

Having achieved the synthesis of the four monomeric units, we next proceeded to couple them to achieve the synthesis of the desired conjugatable aminophenyl tetra-saccharide 2a. The 3+1 strategy, wherein the monomers were assembled in the order of the glucosmainyl residue, the fucosyl residue, the galactosyl residue, and finally the sialyl residue, provided the most effective and acceptable synthetic route Scheme 4

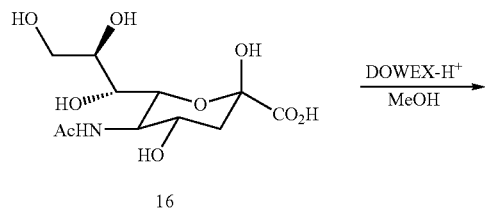

16 i) Glycosylation of the Protected Glucosamine with the Protected Fucosyl Bromide to Obtain the Disaccharide Unit 21

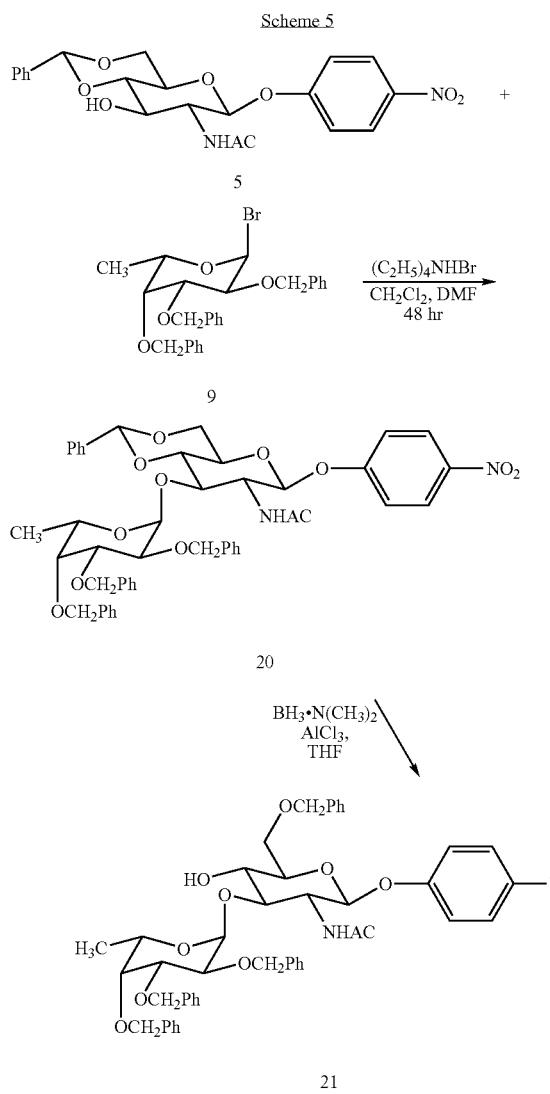

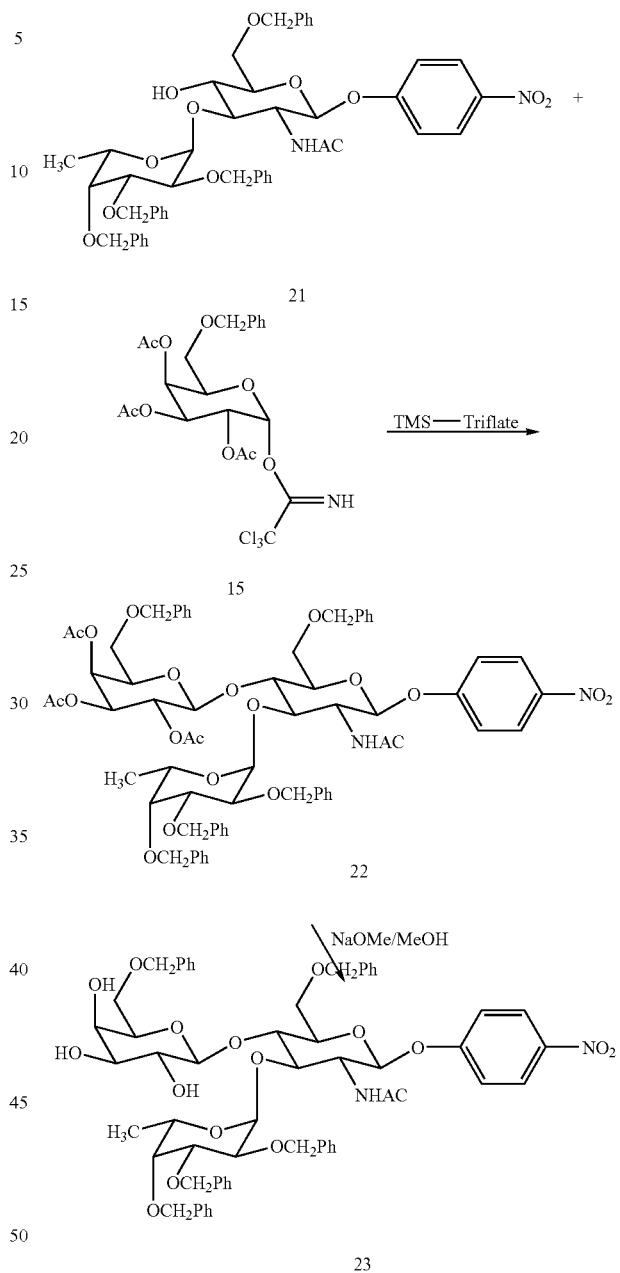

Scheme 5 depicts the synthesis of the disaccharide unit 21. 4-Nitrophenyl 2-acetamido-4,6-benzylidene-2-deoxy-β-D-gluocopyranoside (compound 5) was coupled with 2,3,4-O-tribenzyl-α-fucopyranosyl bromide (compound 9) in the presence of TEAB and molecular sieve 4 Å in a mixture of DMF and $CH_2Cl_2$ to obtain the disaccharide 20 in 69% yield. The proton NMR signal of the fucose unit in the disaccharide 20 at δ 5.06 established the anomeric configuration to be α. Cleavage of the acetal ring of compound 20, with simultaneous reduction of the intermediate hemiacetal, by treatment with $BH_3$—$NMe_3$ in the presence of $AlCl_3$ in THF gave the orthogonally protected 4-nitrophenyl 6-O-benzyl-2-deoxy-2-acetamido-(3→1)-(2,3,4-tri-O-benzyl-α-L-fucopyrano-syl)-β-D-glucopyranoside (compound 21) in 50% yield.

ii) Glycosylation of the Disaccharide 21 with the Protected Galactopyranosyl Trichloroactimidate to Obtain the Trisaccharide 23

The trisaccharide unit 23 was prepared as shown in Scheme 6. A solution of 4-nitrophenyl 6-O-benzyl-2-deoxy-2-acetamido-(3→1)-(2,3,4-tri-O-benzyl-α-L-fucopyranosyl)-β-D-glucopyranoside (compound 21) and 2,3,4-tri-O-acetyl-6-O-benzyl-α-D-galactopyranosyl trichloroacetimidate (compound 15) in $CH_2Cl_2$ was treated with TMS-OTf at −5° C. for 1 h and at 0° C. for 48 h to obtain 4-nitrophenyl 6-O-benzyl-2-deoxy-2-acetamido-(4→1)-(6-O-benzyl-2,3,4-tri-O-acetyl-β-D-galctopyranosyl)-(3→1)-(2,3,4-tri-O-benzyl-α-L-fucopyranosyl)-β-D-glucopyranoside (compound 22) in 63% yield. Deacetylation with NaOMe in methanol afforded 4-nitrophenyl 6-O-benzyl-2-deoxy-2-acetamido-(4→1)-(6-O-benzyl-β-D-galctopyranosyl)-(3→1)-(2,3,4-tri-O-benzyl-α-L-fucopyranosyl)-β-D-glucopyranoside (compound 23) in 89% yield.

iii) NIS-TMS-Otf Promoted Glycosylation of the Trisaccharide 23 with the Protected Thiophenyl Sialic Acid Methyl Ester Unit to Obtain the Tetrasaccharide 25 galactopyranosyl)-(3-1)-(2,3,4-tri-O-benzyl-(α-L-fucopyranosyl)-β-D-glucopyranoside (compound 23) in acetonitrile was cooled to −40° C. and then treated with NIS

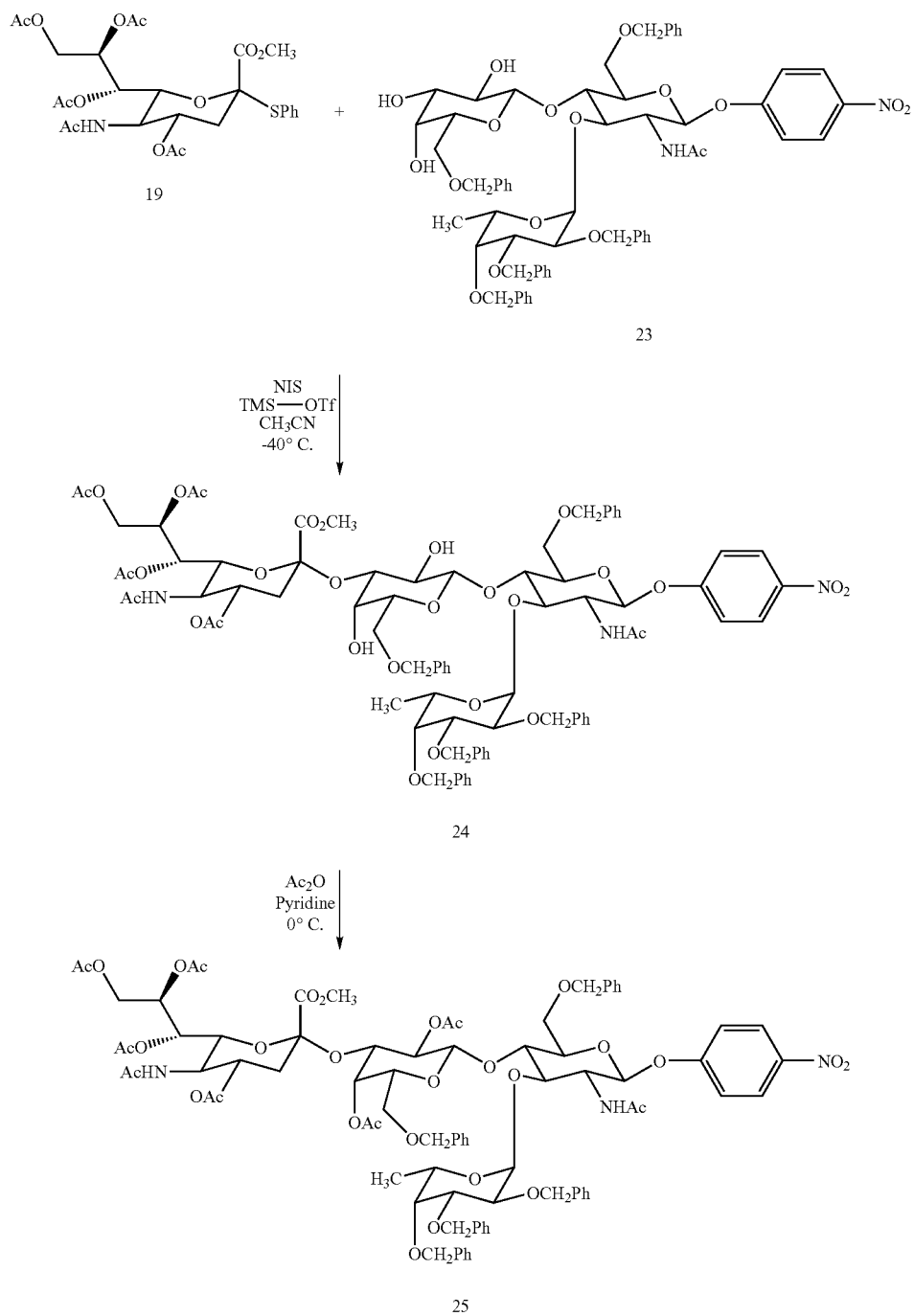

The final coupling to achieve the synthesis of the tetrasaccharide unit 25 was accomplished as shown in Scheme 7. A solution of methyl 5-acetamido-4,7,8,9-tetra-O-acetyl-3,5-dideoxy-S-phenyl-2-thio-D-glycero-D-galacto-2-nonulopyronosuronate (compound 19) and 4-nitrophenyl 6-O-benzyl-2-deoxy-2-acetamido-(4-1)-(6-O-benzyl-β-D- and TMS-OTf to obtain 4-nitrophenyl(methyl 5-acetamido-4,7,8,9-tetra-O-acetyl-3,5-dideoxy-α-D-glycero-D-galacto-2-nonulopyranosuronate)-(2→3)-(6-O-benzyl-β-D-galactopyranosyl)-(1→4)-(2,3,4-tri-O-benzyl-α-L-fucopyranosyl)(1→3))-2-acetamido-6-O-benzyl-2-deoxy-β-D-glucopyranoside (compound 24) in 65% yield. It is noteworthy that the least hindered of the three hydroxyl groups reacted nearly exclusively to form the desired glycosyl linkage. This observation is in conformity with what has been reported[21] by Terada et al., *J. Carbohydr. Chem.*, 8:285 (1989). Acetylation with $Ac_2O$ in pyridine at 0° C. furnished the desired 4-nitrophenyl(methyl 5-acetamido-4,7,8,9-tetra-O-acetyl-3,5-dideoxy-α-D-glycero-D-galacto-2-nonulopyranosuronate)-(2→3)-(6-O-benzyl-2,4-di-O-acetyl-β-D-galactopyranosyl)-(1→4)-(2,3,4-tri-O-benzyl-α-L-fucopyranosyl) (1→3))-2-acetamido-6-O-benzyl-2-deoxy-β-D-glucopyranoside (25) in 78% yield.

c. De-protection and Re-protection of the Functional Groups in Compound 25 for Effective N Conjugation of the Tetrasaccharide Unit ecule is desirable. This objective was realized by following the approach shown in Scheme 8.

The mixed protected tetrasaccharide 25 was hydrogenated over Raney Nickel in methanol at 50 psi and the resulting amine product was treated with Boc-carbonate and $Et_3N$ in THF to obtain the carbamate 26 in 75% yield. Catalytic hydrogenolytic debenzylation of compound 26 over $Pd(OH)_2$ in a mixture of methanol and acetic acid, followed by acetylation with $Ac_2O$ in the presence of $Et_3N$ furnished the peracetylated carbamate 27 in 86% yield. TFA deprotection of compound 27 in $CH_2Cl_2$ afforded the desired conjugatable, protected, Sialyl Lewis[x] analog 2a in 99% yield. Further acetylation using acetyl chloride in $CH_2Cl_2$ in the presence of

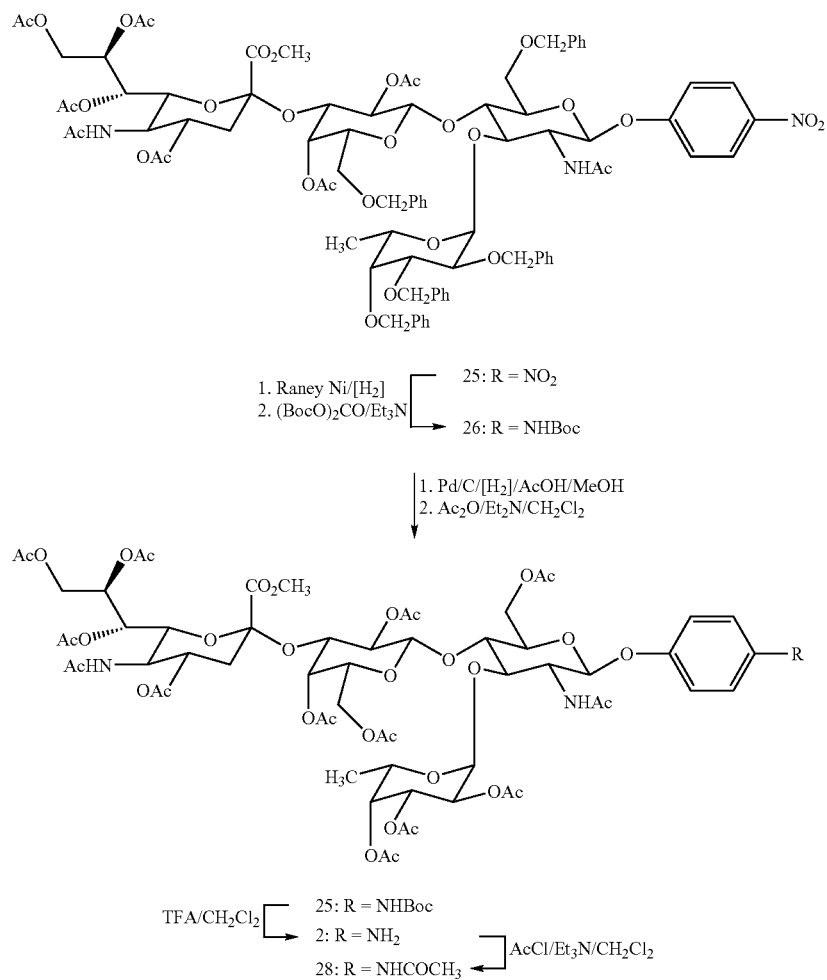

Scheme 8

The tetrasaccharide unit 25 has both base-labile ester protective groups as well as base-stable benzyl protective groups. This arose because of the nature of the chemistry that was carried out and because monomers with certain protective groups only were readily available. Our intention was to be able to eventually reduce the nitro group and use the resulting amino group for conjugation to multi-functional scaffolds. To achieve this goal, a uniform base labile protective groups on all the hydroxyls, viz., per-acetyl protection, in the final mol- $Et_3N$ gave the corresponding acetamide 28 in 86% yield, demonstrating that conjugation with activated electrophilic agents is readily feasible.

d. Conversion of the Peracetylated acetamido-phenyl Sialyl Lewis[x] Ester Analog into the Fully Deprotected Sialyl Lewis[x] Acid 3a The method of deprotection of the peracetylated derivative 28 is shown in Scheme 9. Zemplin deacetylation by first treatment with sodium methoxide in methanol, followed by treatment with water under alkaline conditions, readily afforded the desired 4-(acetamido)phenyl(5-acetamido-3,5-dideoxy-α-D-glycero-D-galacto-2-nonulopyranosuronic acid)-(2→3)-(β-D-galactopyranosyl)-(1→4)-(α-L-fucopyranosyl) (1→3))-2-acetamido-2-deoxy-β-D-glucopyranoside (compound 3a) in 83% yield. This conjugatable tetrasaccharide was 100% pure by reversed phase HPLC and was fully characterized by high-resolution mass spectrometry and NMR data.

A mixture of p-nitrophenyl-2-acetamido-2-deoxy-β-D-glucopyranoside (compound 4) (10.0 g, 30 mmol), benzaldehyde dimethylacetal (10.0 g) and PTS.H$_2$O (0.18 g) in DMF (50 mL) was stirred at 50° C. for about 3 h. TLC of the reaction mixture indicated complete conversion of the starting material to the benzylidine derivative. The mixture was cooled to RT and slowly added to a stirred ice-water (700

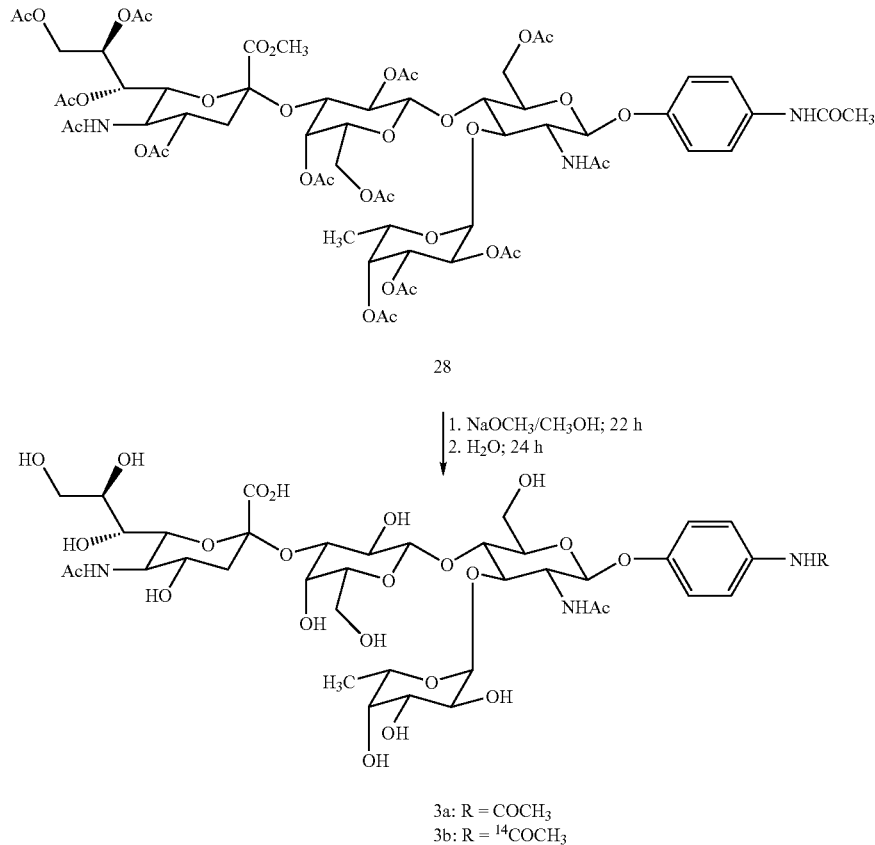

e. Synthesis of $^{14}$C-acetamido-phenyl Sialyl Lewis$^x$ Acid 3b

Following the procedures described herein for the synthesis of the acetamido-phenyl analog 3a, but by substituting CH$_3$$^{14}$COCl for acetyl chloride in the penultimate N-acetylation step, Vitrax Co. (660 S. Jefferson St., Placentia, Calif. 92670) custom synthesized for us the radiolabeled analog 3b. The chemical purity of the product was >99%, the radiochemical purity >99%, and the specific activity 50 mCi/mmol.

EXAMPLE 1

Synthesis of p-Nitrophenyl 2-acetamido-4,6-benzylidine 2-deoxy-β-D-glucopyranoside (Compound 5)

The preparation of this compound was conducted as described in J. Roger, et al., *Carbohydrate Res.*, 6:184-196 (1968), and is given below.

mL). The white solid formed was collected by filtration, washed with water and dried in vacuo to give p-nitrophenyl 2-acetamido-4,6-benzylidine 2-deoxy-β-D-glucopyranoside (compound 5) (12.2 g, yield 97%). TLC analysis (silica gel, 5% MeOH in CH$_2$Cl$_2$) showed a single spot (R$_f$ 0.5, compared to 0.25 for the starting material) thus indicating that the product was essentially pure. This material was used as such for the next step. MS: (M+Na)$^+$=454; $^1$H-NMR (CDCl$_3$-DMSOd$_6$): 1.91 (s, 3 H, NCOCH$_3$), 3.5-4.0 (m, 5 H), 4.32 (dd 1 H), 5.05 (bs, 1 H, OH), 5.42 (d, 1 H, J=7.62 Hz, C$_1$—H), 5.58 (s, 1 H, CH(Ph), 7.16 (d 2 H, J=9.38, Ar—H,), 7.36 (m, 3 H, Ar—H), 7.49 (m, 2 H, Ar—H), 8.18 (d, 2 H, J=9.38 Hz, Ar—H,). When the spectrum was run in 100% DMSO-d$_6$, the OH proton appears as a doublet at 5.61 (J=4.69 Hz) and the benzylidine proton (OCHO) was slightly shifted downfield at 5.73 (s).

EXAMPLE 2

Synthesis of 2,3,4-Tri-O-benzyl-1-O-p-nitrobenzoyl-α-L-fucopyranose (Compound 8)

The preparation of this compound was conducted as described in M. Dejter-Juszynski and H. M. Flowers, *Carbohydrate Res.*, 1.8:219-216 (1971), and is given below.

To a cooled solution (5° C.) of 2,3,4-tri-O-benzyl-L-fucopyranose (compound 6) (6.0 g, 13.45 mmol) in dry $CH_2Cl_2$ (100 mL) was added pyridine (7.5 mL) followed by a slow addition of p-nitrobenzoyl chloride (compound 7) (3.15 g, 17 mmol) in portions over a 5 min period. After the addition, the mixture was stirred at 5° C. for 5-10 min then at RT for 18 h. The mixture was diluted with $CH_2Cl_2$ (100 mL) and the solution was washed successively with cold 1N HCl, water, cold aqueous $NaHCO_3$, water, dried and concentrated to give a gummy product (9.0 g). TLC analysis (silica gel, hexane-EtOAc 3:1) indicated the presence of a major ($R_f$ 0.6) and a minor ($R_f$ 0.48) product, but no starting material. This could be due to a mixture of α and β isomers, which seemed to separate if present as their esters. The product was chromatographed over a column of silica gel (400 g) eluting with 5-30% EtOAc in hexane and collecting 50 mL fractions. Fractions 65-75 furnished 2,3,4-tri-O-benzyl-1-O-p-nitrobenzoyl-α-L-fucopyranose as a gummy material (6.7 g, yield 85%). Fractions 80-96 furnished 2,3,4-tri-O-benzyl-1-O-p-nitrobenzoyl-β-L-fucopyranose (1.13 g, yield 15%).

Since both the α and β isomers yielded the same β-bromide (compound 9), it was decided to skip the column purification and instead use the mixture as such. In this case, 2,3,4-tri-O-benzyl-L-fucopyranose (compound 6) (25 g, 55 mmol) was treated with p-nitrobenzoyl chloride (compound 7) as described above and the crude material (33.0 g) was dissolved in $CH_2Cl_2$ (100 mL) and simply filtered through a short column of silica gel. This removed the color and other polar material. This procedure furnished the anomeric mixture of esters (compound 8) as a gummy material (25.7 g, yield 80%).

Properties of the α isomer: TLC: $R_f$ 0.6 (α-isomer); silica gel, Hexane-EtOAc 3:1).

MS (ESI): m/z 601.3 $(M+NH_4)^+$; $^1$H-NMR ($CDCl_3$): 1.18 (d, 3H, J=6.45 Hz, $CH_3$), 3.78 (d, 1H, —$C_2H$—O), 3.98-4.09 (m, 2 H, —CHO), 4.29 (dd, 1 H, J=3.52 Hz, J=9.97 Hz, OCH—), 4.70-5.10 (m, 6 H, $CH_2Ph$), 6.60 (d, 1H, J=3.5 Hz, $C_1$—H), 7.2-7.5 (1SH, m, Ar—H), 8.12 (d, 2 H, Ar—H), 8.27 (d, 2 H, Ar—H); $^{13}$C-NMR ($CDCl_3$): 16.67 ($CH_3$), 69.8 (CH), 72.94 ($OCH_2Ph$), 73.34 ($OCH_2Ph$), 74.96 ($OCH_2Ph$), 75.16 (OCH), 77.00 (OCH), 78.47 (OCH), 92.84 (O—CH—O), 123.51, 127.54, 127.71, 127.83, 128.29, 128.37, 130.82, 135.6, 137.9, 138.2, 138.3 (aromatic carbons), 150.6 (ArC—$NO_2$), 163.30 (C=O).

Properties of the β isomer: TLC: 0.48 (β-isomer) (Silica gel, Hexane-EtOAc 3:1); MS (ESI): m/z 601.3 $(M+NH_4)^+$; $^1$H-NMR ($CDCl_3$): 1.21 (d, 3 H, J=6.45 Hz, $CH_3$), 3.71 (m, 3 H, OCH), 4.72-5.05 (m, 6 H, $CH_2Ph$), 5.82 (d, 1 H, J=7.62 Hz, C1—H), 7.18-7.41 (m, 15H, Ar—H), 8.12 (m, 2H, d, J=8.8 Hz, ArH), 8.24 (d, 2 H, J=8.8 Hz, ArH). $^{13}$C-NMR ($CDCl_3$): 16.73 ($CH_3$), 71.85 (OCH), 73.14 (OCH2), 74.84 (OCH2), 75.27 (OCH2), 75.82 (OCH), 77.60 (OCH), 82.96 (OCH), 95.35 ($OC_1$—O), 123.45, 127.66, 127.86, 128.00, 128.15, 128.32, 128.55, 131.17, 138.05, 138.20 (aromatic carbons), 150.72 (aromatic C—$NO_2$), 163.28 (C=O).

EXAMPLE 3

Synthesis of 2,3,4-tri-O-benzyl-α-L-fucopyranosyl Bromide (Compound 9)

The preparation of this compound was conducted as described in M. Dejter-Juszynski and H. M. Flowers, *Carbohydrate Res.*, 18:219-216 (1971), and is given below.

A saturated solution of HBr in $CH_2Cl_2$ (20.0 mL) was prepared by passing anhydrous HBr in $CH_2Cl_2$ at 0° C. for 30 min. This solution was added to a cold solution of the α-isomer of the 2,3,4-tri-O-benzylfucopyranose-p-nitrobenzoate (compound 8) (6.5 g, 11 mmol) in $CH_2Cl_2$ (150 mL) at 0-5° C., and the mixture was stirred at 5° C. for 30-40 min. The precipitated p-nitrobenzoic acid was filtered off, and the filtrate was successively washed with cold sat. $NaHCO_3$ and water until neutral. The extract was dried ($MgSO_4$) and the solvent removed at RT in vacuo to afford exclusively the α-fucopyranosyl bromide as a highly viscous liquid (5.3 g, yield 95%).

Similarly, treatment of the β-isomer of the fucopyranosyl-p-nitrobenzoate (compound 8) (583 mg, 1 mmol) with a saturated solution of HBr in $CH_2Cl_2$ (5 mL) for 30 min at 5° C. furnished the α-fucopyranosyl bromide (550 mg). The NMR spectrum of this product was identical with that of α-bromide obtained earlier from the α-fucopyranosyl p-nitrobenzoate. However, due to the instability of the bromide, it was used as such immediately for the next step. $^1$H-NMR ($CDCl_3$): 1.17 (d, 3H, J=6.45 Hz, $CH_3$), 3.6-4.2 (m, OCH), 4.8-5.02 (m, $OCH_2$), 6.53 (d, 1H, OCHBr), 7.2-7.5 (15H, Ar—H); $^{13}$C-NMR ($CDCl_3$): 16.61 ($CH_3$), 72.36 (OCH), 73.23 ($OCH_2$), 74.00 ($OCH_2$), 75.59 ($OCH_2$), 76.57 (OCH), 74.49 (OCH), 80.02 (OCH), 95.26 (OCHBr), 127.97, 128.09, 128.23, 128.32, 128.43, 128.75, 128.86 (aromatic carbons).

EXAMPLE 4

Synthesis of 2-(Trimethylsilyl)ethyl-2,3,4,6-tetra-O-acetyl-β-D-galactopyranoside (Compound 11)

The preparation of this compound was conducted as described in K. J. Ahlfors, et al., *J. Org. Chem.*, 53:5629-5647 (1998), and is given below.

To a mixture of acetobromo α-D-galactose (10) (25 g, 60 mmol), 1-(trimethylsilyl)ethanol (10.72 g, 13.0 mL, 91 mmol), and $CaSO_4$ (20 g) in $CH_2Cl_2$ (500 mL) at 0° C. were added red mercuric oxide (13.2 g) and mercuric bromide (500 mg). The red slurry was then stirred at RT for 48 h. The inorganic salts were filtered and the $CH_2Cl_2$ solution was washed with aqueous $NaHCO_3$, water and dried ($Na_2SO_4$). Evaporation of the solvent gave a thick viscous oil. This was purified by column chromatography (silica gel, hexane-ethyl acetate, 9:1, 8:2, 7:3). Fractions containing the compound were collected and the solvent was evaporated to obtain compound 11 as a thick oil. (20.0 g, yield 73.5%). $^1$HNMR ($CDCl_3$): 0.01(s, 9 H, Si $Me_3$), 0.98 (m, 2 H, $CH_2CH_2Si$), 1.96, 2.03 and 2.12 (s, 9 H, $COCH_3$), 3.57 and 3.99 (m, 2 H, $CH_2CH_2Si$), 3.90 (m, 1H, H-5), 4.13 and 4.20 (dd, 2 H, H-6), 4.48 (d, 1 H, J=7.8 Hz, H-1) 5.01 (dd, 1 H, H-3), 5.20 (dd, 1 H, H-2), 5.39 (dd, 1 H, H-4). MS: $(M+Na)^+$=471.5.

EXAMPLE 5

Synthesis of 2-(Trimethylsilyl)ethyl-β-D-galactopyranoside (Compound 11a)

The preparation of this compound was conducted as described in K. J. Ahlfors, et al., *J. Org. Chem.*, 53:5629-5647 (1998), and is given below.

A solution of 2-(trimethylsilyl)ethyl 2,3,4,6-tetra-O-acetyl-β-D-galactopyranoside (compound 11) (20.0 g, 44.6 mmol) in methanol (150 mL) was added to a methanolic solution of sodium methoxide (from 200 mg sodium in methanol 200 mL) and stirred at RT for 3 h. The reaction mixture was then neutralized with Dowex 50×8-400 ion-exchange (H$^+$) resin and filtered. Methanol was evaporated and the residue was dissolved in ether (500 mL) and left at RT for 15 min. The precipitated solid was filtered and dried under vacuum to obtain the compound 11a. (12.0 g, yield 96%). $^1$HNMR (D$_2$O) 0.01(s, 9 H, SiMe$_3$), 1.02 (m, 2 H, CH$_2$CH$_2$Si), 3.44 (dd, 1 H, H-2), 3.57 and 3.99 (m, 2H, CH$_2$CH$_2$Si), 3.59 (dd, 1 H, H-3), 3.78(m,5H, H-6). 3.88 (dd, 1 H-4), 4.35 (d, 1 H, H-1); MS: (M+Na)$^+$=303.1.

EXAMPLE 6

Synthesis of 2-(Trimethylsilyl)ethyl 4,6-O-benzylidene-β-D-galactopyranoside (Compound 12)

The preparation was conducted as described in K. J. Ahlfors, et al., *J. Org. Chem.*, 53: 5629-5647 (1998) and is given below.

To a solution of 2-(trimethylsilyl)ethyl-β-D-galactopyranoside (28.0 g, 100 mmol) and benzaldehyde dimethyl acetal (18.24 g, 120 mmol) in DMF (60 mL) PTS (500 mg) was added and the mixture heated at 50° C. for 16 h. DMF was removed under vacuum and the product dissolved in ethyl acetate (200 mL), washed with aqueous NaHCO$_3$, water and dried (Na$_2$SO$_4$). Removal of ethyl acetate afforded 2-(trimethylsilyl)ethyl 4,6-O-benzylidene-β-D-galactopyranoside (compound 12) as a glassy solid. (24.0 g, yield 87%). This was used in the next step without further purification. $^1$HNMR (CDCl$_3$): 0.02 (s, 9 H, SiMe$_3$), 0.98 (m, 2 H, CH$_2$CH$_2$Si), 3.57 and 3.99 (m, 2 H, CH$_2$CH$_2$Si), 3.42 (br s, 1 H, H-5), 3.65 (dd, 1 H, H-3), 3.72 (dd, 1 H, H-2), 4.05 (dd, 1 H, H-6), 4.27 (d, 1 H, H-1), 4.16 (dd, 1 H, H-4) 4.31 (dd, 1 H, H-6), 5.52 (s, 1 H, PhCH), 7.25 and 7.5 (m, 5 H, ArH); MS: (M+Na)$^+$=391.5

EXAMPLE 7

Synthesis of 2-(Trimethylsilyl)ethyl-2,3-di-O-acetyl-4,6-O-benzylidene-β-D-galactopyranoside (Compound 13)

Acetic anhydride (100 mL) was added to a solution of 2-(trimethylsilyl)ethyl-4,6-O-benzylidene-β-D-galactopyranoside (compound 12) (23.0 g, 62.5 mmol) in pyridine (100 mL) and the mixture was stirred at RT for 16 h. Pyridine and acetic anhydride were removed under vacuum. Toluene (4×75 mL) was added and evaporated from the residue to remove traces of pyridine and acetic anhydride. The residue was chromatographed over silica gel (7:3 hexane/ethyl acetate) to give 2-(trimethylsilyl)ethyl-2,3-di-O-acetyl-4,6-O-benzylidene-β-D-galactopyranoside (compound 13) as a syrup. (23.0 g, yield 82%). $^1$HNMR (CDCl$_3$): 0.03(s, 9 H, SiMe$_3$), 0.98 (m, 2 H, CH$_2$CH$_2$Si), 2.05 (s, 6 H, COCH$_3$), 3.5 (bs, 1 H, H-5), 3.57 and 4.05 (m, 2 H, CH$_2$CH$_2$Si), 4.1 (dd, 1 H, H-6), 4.42 (dd, 1 H, H-2), 4.52 (d, 1 H, J=7.8 Hz, H-1), 4.95 (dd, 1 H, H-3), 5.38 (dd, 1 H, H-4), 5.5 (s, 1 H, CHPh), 7.32-7.58 (m, 5 H, ArH); MS: (M+Na)$^+$=475.

EXAMPLE 8

Synthesis of 2-(Trimethylsilyl)ethyl 2,3,4-tri-O-acetyl-6-O-benzyl-β-D-galactopyranoside (Compound 14)

Molecular sieve 4 Å (AW-300, 5 g) was added to a solution of 2-(trimethylsilyl)ethyl-2,3-di-O-acetyl-4,6-O-benzylidene-β-D-galactopyranoside (13) (4.97 g, 11 mmol) in anhydrous THF (25 mL) and the mixture was stirred at RT for 1 h. BH$_3$—NMe$_3$ complex (4.8 g, 6 mmol) was then added and the reaction mixture was stirred at RT for a further 30 min. The solution was then cooled (0° C.) and anhydrous aluminum chloride (8.8 g, 6 mmol) was added in two portions. The reaction mixture became exothermic during the addition of aluminum chloride and the stirring was continued at RT. When the TLC (CH$_2$Cl$_2$-EtOAc, 8:2) indicated the completion of the reaction (4 h), the mixture was filtered and the filtrate was treated with Dowex 50 (H$^+$) resin, filtered, and concentrated. The residue was co-evaporated with methanol (3×100 mL). The syrupy residue was dissolved in water (40 mL) and extracted with ethyl acetate (3×75 mL). Evaporation of ethyl acetate gave a thick oil, which was chromatographed over silica gel (CH$_2$Cl$_2$-EtOAc, 8:2). Fractions containing the desired compound were combined and the solvent removed to obtain of 2-(trimethylsilyl)ethyl-2,3-di-O-acetyl-6-O-benzyl-β-D-galactopyranoside (2.45 g, yield 49%)). A solution of this product (2.48 g) in pyridine (10 mL) was treated with acetic anhydride (10 mL) and allowed to stir at RT overnight. Toluene (3×50 mL) was added and evaporated from the residue to remove traces of pyridine and acetic anhydride. The residue was chromatographed over silica gel (7:3 hexane: ethyl acetate) to obtain 2-(trimethylsilyl)ethyl-2,3,4-tri-O-acetyl-6-O-benzyl-β-D-galactopyranoside (compound 14) as a colorless oil (2.43 g, yield 90%). $^1$HNMR (CDCl$_3$): 0.03 (s, 9 H, SiMe$_3$), 0.98 (m, 2 H, CH$_2$CH$_2$Si), 1.98, 2.01, 2.05 (s, 9 H, COCH$_3$), 3.5 (bs, 1 H, H-5), 3.57 and 4.05 (m, 2 H, CH$_2$CH$_2$Si), 4.1 (dd, 1 H, H-6), 4.42 (dd, 1 H, H-2), 4.48 (d, 1 H, J=7.8 Hz, H-1), 5.03 (dd, 1 H, H-3), 5.20 (dd, 1 H, H-2), 5.39 (dd, 1 H, H-4), 4.5 (q, 2 H, CH$_2$Ph), 7.32-7.58 (m, 5 H, ArH); MS: (M+Na)$^+$=518.9.

EXAMPLE 9

Synthesis of 2,3,4-tri-O-acetyl-6-O-benzyl-α-D-galactopyranosyl Trichloroacetimidate (Compound 15)

To a stirred solution of 2-(trimethylsilyl)ethyl-2,3,4-tri-O-acetyl-6-O-benzyl-β-D-galactopyranoside (compound 14) (4.96 g, 10 mmol) in CH$_2$Cl$_2$ (100 mL) cooled to 0° C., was added TFA (7.5 mL). The reaction mixture was allowed to warm to RT and then stirred for 18 h. CH$_2$Cl$_2$ and TFA were removed on a rotary evaporator and the residue was co-evaporated with toluene (3×25 mL). The product was dissolved in CH$_2$Cl$_2$ and treated with a saturated solution of NaHCO$_3$ (5 mL). The organic layer was dried (Na$_2$SO$_4$), concentrated, dried under vacuum for 24 h to obtain 2,3,4-tri-O-acetyl-6-O-benzyl-α-D-galactopyranose (compound 14a) (3.7 g, yield 94%; MS: (M+Na)$^+$=419.1). This product was used in the following step without further purification.

To a cooled (−5° C.) solution of 2,3,4-tri-O-acetyl-6-O-benzyl-O-D-galactopyranose (compound 14a) (3.7 g, 9.3 mmol) in CH$_2$Cl$_2$ (50 mL), were added trichloroacetonitrile (4.5 mL) and DBU (250 mL). The mixture was stirred at 0° C. for 1 h and at RT for 3 h. The mixture was concentrated to a syrup and then chromatographed over silica gel (hexane ETOAc, 7:3) to obtain 2,3,4-tri-O-acetyl-6-O-benzyl-α-D-galactopyranosyl trichloroacetimidate (compound 15) as an amorphous solid (3.8 g, yield 80%). $^1$HNMR (CDCl$_3$): 2.00, 2.01 2.05 (s, 9 H, COCH$_3$), 4.5 (dd, 2H, CH$_2$Ar), 6.58 (d, 1H, J=3.5 Hz, H-1), 7.29 (m, 5H. ArH), 8.63 (s, 1H, NH); MS: (M+Na)$^+$=561.8.

EXAMPLE 10

Synthesis of Methyl 5-acetamido-3,5-dideoxy-D-glycero-D-galacto-2-nonulosonate (Compound 17)

The preparation of this compound was conducted as described in R. Kuhn, et al., Chem. Ber., 99:611-617, (1966), and is given below.

To a slurry of 5-acetamido-3,5-dideoxy-D-glycero-D-galacto-2-nonulosonic acid (compound 16) (10 g, 32.36 mmol) in methanol (1000 mL), Dowex H+ 50×8-4-400 ion-exchange resin (30.0 g, washed with methanol and dried in vacuum overnight at 25° C.) was added and the mixture was stirred at RT for 12 h. The reaction mixture was filtered and the resin was washed with methanol (75 mL). The filtrate and the washings were combined, more methanol (500 mL) added and the solution stirred for an additional 1 h at RT. Methanol was removed on a rotary evaporator to yield the methyl ester 17 (10.2 g, yield 98%). MP: 178-179° C. (lit[17] MP 178-180° C.); $^1$H-NMR(DMSO-$d_6$): 1.76 (t, 1H, H-3a), 1.91(s, 3H, NHCOCH$_3$), 2.05 (dd, 1H, H-3e), 4.32 (1H, dd), 5.05 (1H, bs, OH), 5.42 (1H, d, J=7.62 Hz, C$_1$—H), 5.58 (1H, s, O—CH (Ph)—O), 7.16 (2H, d, J=9.38, Ar—H, part of A2B2 system), 7.36 (3H, m, Ar—H), 7.49 (2H, m, Ar—H), 8.18 (2H, d, J=9.38 Hz, Ar—H.

EXAMPLE 11

Synthesis of Methyl 5-acetamido-2,4,7,8,9-penta—O-acetyl-3,5-dideoxy-D-glycero-D-galacto-2-nonulosonate (Compound 18)

The preparation of this compound was conducted as described in M. N. Sharma and R. Eby, Carbohydrate Res., 127:201-210 (1984), and is given below.

To a cooled (0° C.) mixture of dry pyridine (100 mL) and acetic anhydride (100 mL), methyl 5-acetamido-3,5-dideoxy-D-glycero-D-galacto-2-nonulosonate (compound 17) (10 g, 31.0 mmol) was added and the mixture was stirred at 0° C. for 4 h and at RT for 48 h. Pyridine and acetic anhydride were removed under vacuum. Toluene (4×75 mL) was added and evaporated from the residue to remove traces of pyridine and acetic anhydride and the resultant foamy solid was dried under vacuum. It was recrystallized from hexane-ethyl acetate to obtain the peracetylated product 18. (14.7 g, yield 89%). MP: 156-158° C. (lit[18]. MP 157-158° C.); $^1$H-NMR (CDCl$_3$): 2.01, 2.02, 2.04, 2.05, 2.07 (5s, 15 H, 5COCH3), 2.45 (dd, H-3$_{ax}$), 2.62 (dd,$_{J3eq,4}$=5.1 Hz, J$_{gem}$=13.4 Hz, H-3eq-β), 3.78 (s, 3 H, CO$_2$CH$_3$) and 3.80 (s, 3 H, CO$_2$CH$_3$). 4.19 (dd, J$_{8,9}$=7.2 Hz, J$_{9,9'}$=12.6 Hz, H-9), 4.20 (dd, J$_{5,6}$=10.1 Hz, J$_{6,7}$=2.2 Hz, H-6), 4.43 (dd, J$_{8,9'}$=2.4 Hz, H-9'), 4.97 (t, J$_{4,5}$=J$_{5,6}$=10.1 Hz, H-5), 5.15 ((ddd, H-8α), 5.27 (ddd, H-4α), 5.39 (dd, J$_{7,8}$=6.4H-7α) and 5.54 (m, H-8β), 4.90-5.44 (ddd, H-4β). The anomeric ratio (a:b) was estimated from the ratio of the intensities of the methyl ester signals; MS: (M+H)$^+$=534.

EXAMPLE 12

Synthesis of Methyl 5-acetamido-4,7,8,9-tetra-O-acetyl-3,5-dideoxy-S-phenyl-2-thio-D-glycero-D-galacto-2-nonulopyronosuronate (Compound 19)

The preparation of this compound was conducted as described in M. N. Sharma and R. Eby, Carbohydrate Res., 127:201-210 (1984), and is given below:

To a cooled (0° C.) solution of methyl 5-acetamido-2,4,7,8,9-penta-O-acetyl-3,5-dideoxy-D-glycero-D-galacto-2-nonulosonate (compound 18) (10.66 g, 20 mmol) in anhydrous CH$_2$Cl$_2$ (200.0 mL), were added thiophenol (2.2 mL, 20.2 mmol) and boron trifluoride etherate (3.0 mL, 25 mmol), and the mixture was stirred at RT overnight. The reaction mixture was then diluted with CH$_2$Cl$_2$ (200 mL), washed successively with a saturated solution of sodium bicarbonate and water, dried (Na$_2$SO$_4$) and concentrated. The viscous oil obtained was triturated with hexane (300 mL) and the solid formed was filtered and recrystallized from hexane-ethyl acetate to obtain methyl 5-acetamido-4,7,8,9-tetra-O-acetyl-3,5-dideoxy-S-phenyl-2-thio-D-glycero-D-galacto-2-nonulopyronosuronate (compound 19) (1.32 g, yield 92%). MP: 180-82° C. (lit 181-82° C.); $^1$H-NMR (CDCl$_3$): (dd,$_{J3eq,4}$=5.1 Hz, Jgem=13.9 Hz, H-3eq-β), 2.89 (dd, J3eq,4=4.8 Hz, Jgem=12.8 Hz, H-3eq-α), 4.90 (ddd, H-4α), 5.44 (ddd, H-4β), 3.56 (s, 3 H, CO$_2$CH$_3$) and 3.67 (s, 3 H, CO$_2$CH$_3$). The anomeric ratio (a:b) was estimated from the ratio of the intensities of the methyl ester signals. MS: (M+H)$^+$=584.

EXAMPLE 13

Synthesis of 4-Nitrophenyl 4,6-benzylidene-2-deoxy-2-acetamido-(3→1)-(2,3,4 tri-O-benzyl-α-L-fucopyranosyl)-β-D-glucopyranoside (compound 20)

To a stirred mixture of 4-nitrophenyl-2-acetamido-4,6-benzylidine 2-deoxy-β-D-glucopyranoside (compound 5) (4.3 g, 10 mmol), TEAB (2.2 g, 10 mmol) and powdered molecular sieves (4A°, 15 g) in CH$_2$Cl$_2$ (25 mL) and DMF (10 mL), was added a solution of 2,3,4-tri-O-benzyl-α-fucopyranosyl bromide (compound 9) (7.5 g, 15 mmol) in CH$_2$Cl$_2$ (15 mL) and the mixture was stirred for 50 h at room temperature under a nitrogen atmosphere. Methanol (2 mL) was added and the stirring was continued for a further 2 h. The solution was then diluted with CH$_2$Cl$_2$ (100 mL), filtered through a pad of Celite and the filter cake washed with CH$_2$Cl$_2$ (100 mL). The combined filtrates were treated with solid sodium bicarbonate, filtered, and the filtrate concentrated. The pasty residue was triturated with water (100 mL). After stirring overnight (12 h), the solid material was collected and dried. This material was suspended in hexane (300 mL) and stirred for 3-4 h. The resulting solid was collected by filtration and re-suspended in hexane (300 mL) and stirred for 2-3 h. The solid thus obtained was collected and dried (8.45 g). Recrystallization of this material from methanol furnished 4-Nitrophenyl 4,6-benzylidene-2-deoxy-2-acetamido-(3→1)-(2,3,4-tri-O-benzyl-α-L-fucopyranosyl)-β-glucopyranoside (compound 20) as a white solid (5.85 g, yield 69%). TLC: R$_f$ 0.45 (silica gel, CH$_2$Cl$_2$/hexane/MeOH 9/1/0.25); NMR (CDCl$_3$): 0.83 (d, 3H, J=6.41 Hz, CH$_3$), 1.61 (s, 3H, NCOCH$_3$), 3.60-5.00 (m, OCH, OCH2), 5.06 (d, 1H, J=3.5 Hz, C$_1$—H for fucosyl residue), 5.53 (s, 1H, OCHO), 5.68 (d, 1H, J=8.2 Hz, C1-H of glucosamine residue), 7.03 (d, 2H, J=9.38 Hz, Ar—H), 7.20-7.60 (m, Ar—H), 8.17 (d, 2H, d, J=9.38 HzAr—H); MS: (M+H)$^+$=847. Elemental Analysis: Found: C, 68.16; H, 5.89; N 3.22%. Calculated for C$_{48}$H$_{50}$N$_2$O$_{12}$; C, 68.07; H, 5.95; N, 3.31; O, 22.67%.

EXAMPLE 14

Synthesis of 4-Nitrophenyl 6-O-benzyl-2-deoxy-2-acetamido-(3→1)-(2,3,4-tri-O-benzyl-α-L-fucopyranosyl)-β-D-glucopyranoside (Compound 21)

Molecular sieve 4 Å (AW-300, 5 g) was added to a solution of 4-nitrophenyl 4,6-benzylidene-2-deoxy-2-acetamido-(3→1)-(2,3,4-tri-O-benzyl-α-L-fucopyranosyl)-β-D-glucopyranoside (compound 20) (5.0 g, 5.9 mmol) in anhydrous THF (50.0 mL) and the mixture was stirred at RT for 1 h. $BH_3$—$NMe_3$ complex (4.82. g, 36 mmol) was then added and the reaction mixture was stirred at RT for a further 30 min. The solution was then cooled (0° C.) and anhydrous aluminum chloride (5.3 g, 39.8 mmol) was added in two portions. The reaction mixture became exothermic during the addition of aluminum chloride and the stirring was continued at 50° C. When the TLC of the reaction mixture indicated the completion of the reaction (2 h), the mixture was filtered and the filtrate was treated with Dowex 50 ($H^+$) resin, filtered and concentrated. The residue was co-evaporated with methanol (3×100 mL). The syrupy residue was dissolved in water (100 mL) and the precipitated solid was filtered and dried. It was then chromatographed over silica gel ($CH_2Cl_2$-ethyl acetate, 8:2). The fractions containing the desired compound were combined and the solvent was removed to obtain 4-Nitrophenyl 6-O-benzyl-2-deoxy-2-acetamido-(3→1)-(2,3,4-tri-O-benzyl-α-L-fucopyranosyl)-β-D-glucopyranoside (compound 21) (2.52 g, yield 50.4%). MS: $(M+H)^+$=849.

EXAMPLE 15

Synthesis of 4-Nitrophenyl 6-O-benzyl-2-deoxy-2-acetamido-(4→1)-(6-O-benzyl-2,3,4-tri-O-acetyl-β-D-galctopyranosyl)-(3→1)-(2,3,4-tri-O-benzyl-α-L-fucopyranosyl)-β-D-glucopyranoside (Compound 22)

A solution of 4-Nitrophenyl 6-O-benzyl-2-deoxy-2-acetamido-(3→1)-(2,3,4-tri-O-benzyl-α-L-fucopyranosyl)-β-D-glucopyranoside (compound 21) (1.5 g, 1.8 mmol) and 2,3,4-tri-O-acetyl-6-O-benzyl-α-D-galactopyranosyl trichloroacetimidate (compound 15) (1.5 g, 2.8 mmol) in $CH_2Cl_2$ (20.0 mL) was cooled to −5° C. TMS-OTf (30 μL) was added to the solution and stirred at −5° C. for 1 h and at 0° C. for 48 h. The reaction mixture was treated with a saturated solution of $NaHCO_3$ (1 mL), the organic layer separated, and the aqueous layer further extracted with $CH_2Cl_2$ (3×5 mL). The combined organic layers were dried and concentrated. The residue was triturated with ether (15 mL) and the precipitated starting material 21 was filtered off. The filtrate was concentrated and the residue purified by column chromatography (silica gel, $CH_2Cl_2$:EtOAc, 8:2). The fractions containing the product were collected and evaporated to obtain 6-O-benzyl-2-deoxy-2-acetamido-(4→1)-(6-O-benzyl-2,3,4-tri-O-acetyl-β-D-galctopyranosyl)-(3→1)-(2,3,4-tri-O-benzyl-α-L-fucopyranosyl)-β-D-glucopyranoside (compound 22) as a crystalline solid. It was further crystallized from methanol to get the pure product (1.38 g, yield 63%). MS: $(M+NH_4)^+$=1244.5.

EXAMPLE 16

Synthesis of 4-Nitrophenyl 6-O-benzyl-2-deoxy-2-acetamido-(4→1)-(6-O-benzyl-β-D-galctopyranosyl)-(3→1)-(2,3,4-tri-O-benzyl-α-L-fucopyranosyl)-β-D-glucopyranoside (Compound 23)

4-Nitrophenyl 6-O-benzyl-2-deoxy-2-acetamido-(4→1)-(6-O-benzyl-2,3,4-tri-O-acetyl-β-D-galctopyranosyl)-(3→1)-(2,3,4-tri-O-benzyl-α-L-fucopyranosyl)-β-D-glucopyranoside (compound 22) (1.38 g, 1.11 mmol) was dissolved in methanol (100 mL) and the solution was treated with a sodium methoxide solution, made from sodium 100 mg and methanol 5 mL, at room temperature for 6 h. The reaction mixture was neutralized with the ion-exchange resin Dowex $H^+$, filtered, and the filtrate concentrated. The residue was purified by flash chromatography (silica gel, $CH_2Cl_2$: MeOH, 8:2) to obtain 4-Nitrophenyl 6-O-benzyl-2-deoxy-2-acetamido-(4→1)-(6-O-benzyl-β-D-galctopyranosyl)-(3→1)-(2,3,4-tri-O-benzyl-α-L-fucopyranosyl)-β-D-glucopyranoside (compound 23). (1.10 g, yield 89%). TLC: $R_f$=X (silica gel, $CH_2Cl_2$: methanol 8:2); MS: $(M+NH_4)^+$=1118.5.

EXAMPLE 17

Synthesis of 4-Nitrophenyl(methyl 5-acetamido-4,7,8,9-tetra-O-acetyl-3,5-dideoxy-α-D-glycero-D-galacto-2-nonulopyranosuronate)-(2→3)-(6-O-benzyl-2,4-di-O-acetyl-β-D-galactopyranosyl)-(1→4)-(2,3,4-tri-O-benzyl-α-L-fucopyranosyl) (1→3))-acetamido-6-O-benzyl-2-deoxy-β-D-glucopyranoside (compound 25)

Step (i) Synthesis of 4-nitrophenyl(methyl 5-acetamido-4,7,8,9-tetra-O-acetyl-3,5-dideoxy-α-D-glycero-D-galacto-2-nonulopyranosuronate)-(2→3)-(6-O-benzyl-β-D-galactopyranosyl)-(1→4)-(2,3,4-tri-O-benzyl-α-L-fucopyranosyl) (1→3))-2-acetamido-6-O-benzyl-2-deoxy-β-D-glucopyranoside (Compound 24)

To a solution of methyl 5-acetamido-4,7,8,9-tetra-O-acetyl-3,5-dideoxy-S-phenyl-2-thio-D-glycero-D-galacto-2-nonulopyronosuronate (compound 19) (1.6 g, 2.74 mmol) and 4-nitrophenyl 6-O-benzyl-2-deoxy-2-acetamido-(4-1)-(6-O-benzyl-β-D-galactopyranosyl)-(3-1)-(2,3,4-tri-O-benzyl-α-L-fucopyranosyl)-β-D-glucopyranoside (compound 23) (1.0 g, 9.0 mmol) in dry acetonitrile (25.0 mL) was added molecular sieves 4A (1.0 g), and the mixture was stirred for 1 h at RT. The mixture was cooled (−40° C.) with stirring, NIS (1.3 g, 5.8 mmol) and TMS-OTf (0.012 g, 100 μL, 0.54 mmol) added and the stirring continued for 24 h at −40° C. $Et_3N$ (300 μL) was added to the reaction mixture, which was filtered and washed with acetonitrile (5 mL). The filtrate and the washings were combined, concentrated, and extracted with $CH_2Cl_2$ (100 mL) and washed successively with aqueous $Na_2S_2O_7$ and water and then dried ($Na_2SO_4$). The solution was concentrated and the residue chromatographed over silica gel, (6:4 and then 5:5, ether:EtOAc), to obtain 4-nitrophenyl(methyl 5-acetamido-4,7,8,9-tetra-O-acetyl-3,5-dideoxy-α-D-glycero-D-galacto-2-nonulopyranosuronate)-(2→3)-(6-O-benzyl-β-D-galactopyranosyl)-(1→4)-(2,3,4-tri-O-benzyl-α-L-fucopyranosyl) (1→3))-2-acetamido-6-O-benzyl-2-deoxy-β-D-glucopyranoside (compound 24) as a light brown solid (0.98 g, yield 65%).

Step (ii) Acetylation of Compound 24 to Compound 25

To a cooled (0° C.) mixture of dry pyridine (10.0 mL) and acetic anhydride (10.0 mL) compound 24 (1.0 g, 0.63 mmol) was added and the mixture was stirred at 0° C. for 4 h and at RT for 24 h. Pyridine and acetic anhydride was removed under vacuum. Toluene (4×5 mL) was added and evaporated from the residue to remove traces of pyridine and acetic anhydride and the resultant foamy solid was chromatographed over silica gel (ether:EtOAc, 5:5) to obtain 4-nitrophenyl(methyl 5-acetamido-4,7,8,9-tetra-O-acetyl-3,5-dideoxy-α-D-glycero-D-galacto-2-nonulopyranosuronate)-(2→3)-(6-O-benzyl-2,4-di-O-acetyl-β-D-galactopyranosyl)-(1→4)-(2,3,4-tri-O-benzyl-α-L-fucopyranosyl) (1→3))-2-acetamido-6-O-benzyl-2-deoxy-β-D-glucopyranoside (compound 25) (0.82 g, yield 78%). HRMS: Found, (M+Na)=1680.6178; calculated for $C_{85}H_{99}N_3O_{31}$: 1680.6157.

EXAMPLE 18

Synthesis of 4-(N-t-butyloxycarbonylamino)phenyl(methyl 5-acetamido-4,7,8,9-tetra-O-acetyl-3,5-dideoxy-α-D-glycero-D-galacto-2-nonulopyranosuronate)-(2→3)-(6-O-benzyl-2,4-di-O-acetyl-β-D-galactopyranosyl)-(1→4)-(2,3,4-tri-O-benzyl-α-L-fucopyranosyl) (1→3))-2-acetamido-6-O-benzyl-2-deoxy-β-D-glucopyranoside (Compound 26)

To a solution of 4-nitrophenyl(methyl 5-acetamido-4,7,8,9-tetra-O-acetyl-3,5-dideoxy-α-D-glycero-D-galacto-2-nonulopyranosuronate)-(2→3)-(6-O-benzyl-2,4-di-O-acetyl-β-D-galactopyranosyl)-(1→4)-(2,3,4-tri-O-benzyl-β-L-fucopyranosyl) (1→3))-2-acetamido-6-O-benzyl-2-deoxy-β-D-glucopyranoside (compound 25) (498 mg, 0.3 mmol) in methanol was added Raney Nickel (100 mg) and the mixture was hydrogenated at RT at a pressure 50 psi for 16 h. The catalyst was filtered off and methanol removed in vacuo. The residue was dissolved in THF (10 ml), cooled in an ice bath, and Boc-carbonate (100 mg) and Et$_3$N (140 mg) were added to it and the mixture stirred at room temperature for 24 h. The solvents were removed in vacuo and the residue containing the product was purified by column chromatography over silica gel using ethyl acetate and hexane as the eluents. The fractions were analyzed by TLC and those containing the pure product were combined and solvent removed to obtain 4-(N-t-butyloxycarbonylamino)phenyl (methyl 5-acetamido-4,7,8,9-tetra-O-acetyl-3,5-dideoxy-β-D-glycero-D-galacto-2-nonulopyranosuronate)-(2→3)-(6-O-benzyl-2,4-di-O-acetyl-β-D-galactopyranosyl)-(1→4)-(2,3,4-tri-O-benzyl-α-L-fucopyranosyl) (1→3))-2-acetamido-6-O-benzyl-2-deoxy-α-D-glucopyranoside (compound 26) (370 mg, yield 75%). MS:1728 (M+H)$^+$

EXAMPLE 19

Synthesis of 4-(N-t-butyloxycarbonylamino)phenyl(methyl 5-acetamido-4,7,8,9-tetra-O-acetyl-3,5-dideoxy-α-D-glycero-D-galacto-2-nonulopyranosuronate)-(2→3)-(2,4,6-tri-O-acetyl-β-D-galactopyranosyl)-(1→4)-(2,3,4-tri-O-acetyl-α-L-facopyranosyl) (1→3))-2-acetamido-6-O-acetyl-2-deoxy-β-D-glucopyranoside (compound 27)

To a solution of compound 26 (350 mg, 0.2 mmol) in methanol (50 ml) was added acetic acid (2.0 ml) and palladium hydroxide (150 mg) and the mixture was hydrogenated at 50 psi for 48 h. The catalyst was filtered off and the residue was dissolved in CH$_2$Cl$_2$ (15 ml). To this solution, Et$_3$N (1.0 ml) and acetic anhydride (204 mg, 0.2 mmol) were added and the mixture was stirred at RT for 16 h. The reagents and solvents were removed in vacuo, the residue dissolved in CH$_2$Cl$_2$ (25 ml), washed with water (2×15 ml), and dried. Solvent removal gave a colorless solid. This was purified by column chromatography over silica gel using a mixture of CH$_2$Cl$_2$ and methanol as the eluents. The fractions were analyzed by TLC and those containing the desired product were combined and the solvent removed to obtain 4-(N-t-butyloxycarbonylamino)phenyl (methyl 5-acetamido-4,7,8,9-tetra-O-acetyl-3,5-dideoxy-α-D-glycero-D-galacto-2-nonulopyranosuronate)-(2→3)-(2,4,6-tri-O-acetyl-β-D-galactopyranosyl)-(1→4)-(2,3,4-tri-O-acetyl-α-L-fucopyranosyl) (1→3))-2-acetamido-6-O-acetyl-2-deoxy-β-D-glucopyranoside (compound 27) as a colorless solid (260 mg, yield 86%). MS: 1488 (M+H)$^+$.

EXAMPLE 20

Synthesis of 4-(Acetamido)phenyl(methyl 5-acetamido-4,7,8,9-tetra-O-acetyl-3,5-dideoxy-α-D-glycero-D-galacto-2-nonulopyranosuronate)-(2→3)-(2,4,6-tri-O-acetyl-β-D-galactopyranosyl)-(1→4)-(2,3,4-tri-O-acetyl-α-L-fucopyranosyl) (1→3))-2-acetamido-6-O-acetyl-2-deoxy-β-D-glucopyranoside (Compound 28)

Step (i) Synthesis of 4-(amino)phenyl(methyl 5-acetamido-4,7,8,9-tetra-O-acetyl-3,5-dideoxy-α-D-glycero-D-galacto-2-nonulopyranosuronate)-(2→3)-(2,4,6-tri-O-acetyl-β-D-galactopyranosyl)-(1→4)-(2,3,4-tri-O-acetyl-α-L-fucopyranosyl) (1→3))-2-acetamido-6-O-acetyl-2-deoxy-β-D-glucopyranoside (Compound 2a)

A solution of compound 27 (222 mg, 0.15 mmol) in CH$_2$Cl$_2$ (2.0 mL) was treated with TFA (20 ml) and the mixture was stirred for 16 h. CH$_2$Cl$_2$ and TFA were removed in vacuo and the residue was triturated with hexane to afford 4-(amino)phenyl(methyl 5-acetamido-4,7,8,9-tetra-O-acetyl-3,5-dideoxy-α-D-glycero-D-galacto-2-nonulopyranosuronate)-(2→3)-(2,4,6-tri-O-acetyl-β-D-galactopyranosyl)-(1→4)-(2,3,4-tri-O-acetyl-α-L-fucopyranosyl) (1→3))-2-acetamido-6-O-acetyl-2-deoxy-β-D-glucopyranoside (compound 2a) (205 mg, yield 99%).

Step (ii) Acetylation of Compound 2a to Obtain Compound 28

A solution of Compound 2 (28 mg, 0.02 mmol) in CH$_2$Cl$_2$ (2.0 ml) was cooled in an ice bath and treated with acetyl chloride (11 mg, 0.14 mmol) and Et$_3$N (10 mg, 0.075 mmol). The mixture was left stirring for 18 h. The solvents and reagents were removed in vacuo and the residue was filtered through a small column of silica gel (5 g) using methanol and CH$_2$Cl$_2$. The fractions containing the desired compound were combined and solvent removal furnished 4-(acetamido)phenyl(methyl 5-acetamido-4,7,8,9-tetra-O-acetyl-3,5-dideoxy-α-D-glycero-D-galacto-2-nonulopyranosuronate)-(2→3)-(2,4,6-tri-O-acetyl-β-D-galactopyranosyl)-(1→4)-(2,3,4-tri-O-acetyl-α-L-fucopyranosyl) (1→3))-2-acetamido-6-O-acetyl-2-deoxy-β-D-glucopyranoside (compound 28) (25 mg, yield 87%). MS: (M+H)$^+$1430.

EXAMPLE 21

Synthesis of 4-(Acetamido)phenyl(5-acetamido-3,5-dideoxy-α-D-glycero-D-galacto-2-nonulopyranosuronic acid)-(2→3)-(β-D-galactopyranosyl)-(1→4)-(α-L-fucopyranosyl) (1→3))-2-acetamido-2-deoxy-β-D-glucopyranoside (compound 3a)

To a solution of compound 28 (20 mg, 0.014 mmol) in methanol (1.0 ml) was added sodium methoxide (5.4 mg, 0.1 mmol) and the mixture was stirred at room temperature for 22 h. The reaction mixture was cooled and water (0.1 ml) was added and the stirring was continued for 24 h. The pH of the solution was then adjusted to 6 by treatment with Dowex 50 (H$^+$), and the mixture filtered. Solvent removal from the filtrate afforded a colorless solid (11 mg). This was purified by preparative HPLC (Column, Vydac C-18 (semi prep); eluent, 2% methanol in water; flow rate, 4.0 mL/min, detection, UV 254 nm). The fractions were analyzed by analytical HPLC and those containing the desired product were combined and freeze dried to obtain 4-(acetamido)phenyl(5-acetamido-3,5-dideoxy-α-D-glycero-D-galacto-2-nonulopyranosuronic acid)-(2→3)-(β-D-galactopyranosyl)-(1→4)-(α-L-fucopyranosyl) (1→3))-2-acetamido-2-deoxy-β-D-glucopyranoside (compound 3a) as a colorless solid (7 mg, yield 52%).

HPLC: Retention Time: 9.9 min (column, Vydac C-18, 4.6× 25 cm; Eluent, 0-60% $CH_3CN$ over 60 min; flow rate, 1.0 ml/min; detection, UV 254 nm); HRMS: Found: 954.3453; Calculated for $C_{39}H_{59}N_3O_{24}$: 954.3566

EXAMPLE 22

Synthesis of 4-($^{14}C$-Acetamido)phenyl(5-acetamido-3,5-dideoxy-α-D-glycero-D-galacto-2-nonulopyranosuronic acid)-(2→3)-(β-D-galactopyranosyl)-(1→4)-(α-L-fucopyranosyl) (1→3))-2-acetamido-2-deoxy-β-D-glucopyranoside (Compound 3b)

The $^{14}C$-radiolabeled compound 3b was prepared by VITRAX Co. (660 S. Jefferson St., Placentia, Calif.) following exactly the procedure described for compound 3a except that $CH_3COCl$ was replaced by $CH_3{}^{14}COCl$. HPLC: Retention Time: 4.008 and 4.200 min (column, Microsorb C-18, 5 μM×25 cm; Eluent, water:MeOH [97:3]; flow rate, 1.0 ml/min; detection, radioactivity and UV 240 nm, respectively); Specific Activity: 50 mCi/mmol; Radiochemical Purity: >99% by HPLC; Chemical Purity: >99% HPLC @ 240 nm; Total Activity: 100 μCi; Packaged: 25 mCi/mL H2O:EtOH, [2:1] crimp sealed vial

EXAMPLE 23

Evaluation of Binding Properties of N-acetylated Derivative

We evaluated the ability of the radiolabeled acetamidophenyl Sialyl Lewis$^x$ analog 3b to bind to human aortic endothelial cells in vitro. The analog bound significantly at concentrations in the range 0.1-0.2 mM in activated cells, which is ten fold greater than published value of 1-2 mM for the $K_d$ of native Sialyl Lewis$^x$ (formula A) in vitro. S. A. DeFrees et al., J. Am. Chem. Soc., 117:66-79 (1995). A two-fold increase in the extent of binding was observed in cells stimulated with TNF-α over that obtained in unstimulated control cells. This suggested that E-selectin levels are upregulated in these cells upon TNF-α stimulation. The binding sites were specific to native Sialyl Lewis$^x$, since it was shown that cold unlabeled Sialyl Lewis$^x$ (formula A) at a concentration of 10 mM displaced close to 50% of the bound counts at 0.2 mM concentration. We were thus able to confirm that the conjugatable analog 3b behaved superior to native Sialyl Lewis$^x$ in this E-selectin binding assay.

The above observation reinforces the notion that the binding of monomeric Sialyl Lewis$^x$ analogs to E-selectin is only in the mM range and hence these might be too weak for targeting applications. It would be necessary to attach the monomer to multi-functional scaffolds or to attach it to a phospholipid moiety and form liposomal structures. Such covalently or non-covalently attached multivalent presentations would afford compositions in which the binding strength would have been amplified to a level adequate for targeting applications. The conjugatable 4-aminophenyl Sialyl Lewis$^x$ analog 2a, that we have successfully synthesized, would be eminently suitable for such applications.

ABBREVIATIONS

The following abbreviations have been used herein:
Boc-Carbonate: di-tert-butyl dicarbonate
DBU: 1,8-diazabicyclo[5.4.0]undec-7-ene
DMF: N,N-dimethylformamide
HRMS: high resolution mass spectrum
MP: melting point
MS: mass spectrum
NIS: N-iodosuccinimide
PTS.$H_2O$: p-toluenesulfonic acid hydrate
RT: room temperature
TEAB: tetraethylammonium bromide
TFA: trifluoroacetic acid
THF: tetrahydrofuran
TLC: Thin Layer Chromatography
TMS-OTf: trimethylsilyl trifluromethanesulfonate
TNF-α: Tissue necrosis factor alpha

OTHER EMBODIMENTS

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein. Such equivalents are intended to be encompassed in the scope of the present invention.

All publications and patents mentioned in this specification are herein incorporated by reference.

We claim:

1. A selectin binding ligand conjugate comprising:
   (a) at least one sialyl Lexis X analog (SLewis$^x$) moiety of formula (2);

wherein,
R is a point of attachment for a linker;
R' is hydrogen or acyl; and
R" is hydrogen or methyl
or a pharmaceutically acceptable salt thereof:
   (b) a phospholipid moiety; and
   (c) at least one linker attaching each said SLewis$^x$ moiety to said phospholipid moiety.

2. The conjugate of claim 1, wherein said phospholipid moiety comprises a phospholipid of formula (H):

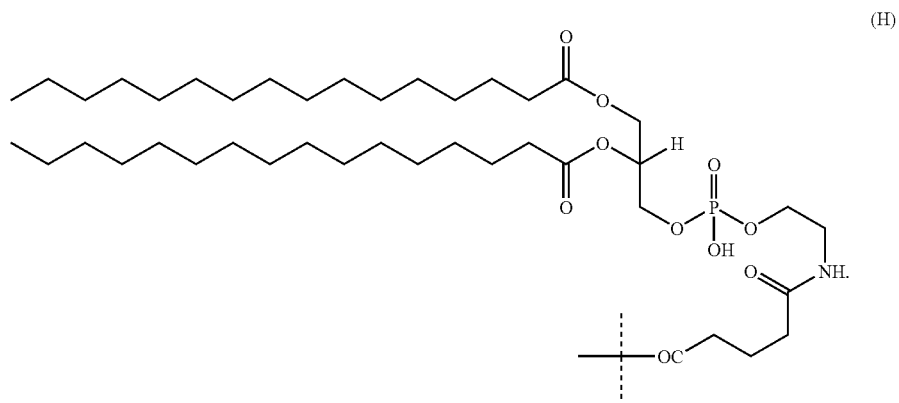

(H)

3. The conjugate of claim 1, wherein said phospholipid moiety comprises a phospholipid of formula (I):

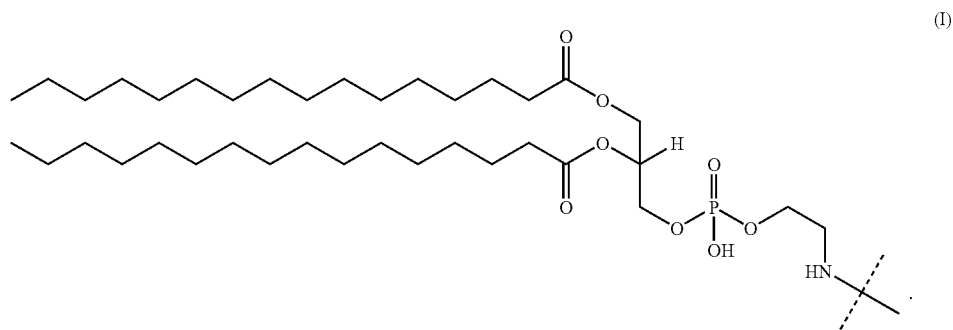

(I)

4. The conjugate of claim 1, wherein said SLewis$^x$ moiety comprises four sialyl Lewis X residues.

5. A pharmaceutical composition comprising the conjugate of claim 1 dissolved or dispersed in a pharmaceutically acceptable carrier.

6. An ultrasound contrast agent comprising the conjugate of claim 1.

7. The ultrasound contrast agent of claim 6, wherein the phospholipid moiety is in the form of a gas-filled microbubble or a gas filled liposome.

8. The ultrasound contrast agent of claim 7, wherein the gas comprises $SF_6$ or a fluorocarbon.

9. The ultrasound contrast agent of any one of claims 8 or 7, further comprising DSPC and/or DPPG.

10. The ultrasound contrast agent of claim 7, wherein the gas comprises $C_4F_{10}$.

11. The ultrasound contrast agent of claim 7, wherein the microbubble or gas-filled liposome further comprises one or more components selected from the group consisting of PEG-4000 and palmitic acid.

12. A method for imaging a region of a patient, said method comprising administering to a patient an effective amount of the contrast agent of claim 7 and imaging a region of the patient.

13. A method for imaging a region of a patient, said method comprising administering to a patient an effective amount of the conjugate of claim 1.

* * * * *